US009758785B2

(12) United States Patent
Anderson et al.

(10) Patent No.: US 9,758,785 B2
(45) Date of Patent: Sep. 12, 2017

(54) MIR-520 MICRORNAS SENSITIZE CANCERS TO PLATINUM-BASED THERAPY

(71) Applicant: BAYLOR COLLEGE OF MEDICINE, Houston, TX (US)

(72) Inventors: Matthew L. Anderson, Houston, TX (US); Claire Mach, Houston, TX (US); Preethi Gunaratne, Houston, TX (US)

(73) Assignees: Baylor College of Medicine, Houston, TX (US); University of Houston, Houston, TX (US)

( * ) Notice: Subject to any disclaimer, the term of this patent is extended or adjusted under 35 U.S.C. 154(b) by 0 days.

(21) Appl. No.: 14/413,894

(22) PCT Filed: Jul. 12, 2013

(86) PCT No.: PCT/US2013/050248
§ 371 (c)(1),
(2) Date: Jan. 9, 2015

(87) PCT Pub. No.: WO2014/011975
PCT Pub. Date: Jan. 16, 2014

(65) Prior Publication Data
US 2015/0159159 A1 Jun. 11, 2015

Related U.S. Application Data

(60) Provisional application No. 61/775,498, filed on Mar. 9, 2013, provisional application No. 61/670,774, filed on Jul. 12, 2012.

(51) Int. Cl.
| | |
|---|---|
| *C12N 15/11* | (2006.01) |
| *C12N 15/113* | (2010.01) |
| *A61K 45/06* | (2006.01) |
| *A61K 31/7088* | (2006.01) |
| *A61K 33/24* | (2006.01) |
| *C07H 21/04* | (2006.01) |
| *A61K 9/00* | (2006.01) |

(52) U.S. Cl.
CPC ...... *C12N 15/1135* (2013.01); *A61K 31/7088* (2013.01); *A61K 33/24* (2013.01); *A61K 45/06* (2013.01); *C12N 15/113* (2013.01); *A61K 9/0019* (2013.01); *C12N 2310/141* (2013.01); *C12N 2320/11* (2013.01); *C12N 2320/31* (2013.01); *C12N 2330/10* (2013.01)

(58) Field of Classification Search
None
See application file for complete search history.

(56) References Cited

U.S. PATENT DOCUMENTS

| 7,709,616 B2 | 5/2010 | Bentwich et al. |
| 2009/0263803 A1 | 10/2009 | Beaudenon et al. |
| 2011/0124712 A1 | 5/2011 | Park et al. |

FOREIGN PATENT DOCUMENTS

| WO | 2011023413 A1 | 3/2011 |
| WO | 2012009508 A2 | 1/2012 |

OTHER PUBLICATIONS

Kim et al., miRNA signature associated with outcome of gastric cancer patients following chemotherapy, 2011, BMC Medical Genomics, vol. 4:79, pp. 1-13.*
Boren et al., MicroRNAs and their target messenger RNAs associated with ovarian cancer response to chemotherapy, 2009, Gynecologic Oncology, vol. 113, pp. 249-255.*
Su et al., miR-520h is crucial for DAPK2 regulation and breast cancer progression, 2015, Oncogene, pp. 1-9.*
Hall et al., The role of cellular accumulation in determining sensitivity to platinum-based chemotherapy, 2008, Annual Review of Pharmacology and Toxicology, vol. 48, pp. 495-535.*
Wang et al., "Circulating MiR-125b as a Marker Predicting Chemoresistance in Breast Cancer" PlosOne, 7 (4): 1-8 (e34210), Apr. 16, 2012, entire document.
To et al., "Escape from hsa-miR-519c enables drug-resistant cells to maintain high expression of ABCG2" Mol Cancer Ther 2009; 8(10) Oct. 2009 pp. 2959-2968.
Su, et al., "Downregulation of MicroRNA miR-520h by E1A Contributes to Anticancer Activity" Cancer Res; 70(12) Jun. 15, 2010, pp. 5096-5108.
Wang, et al., "hsa-miR-520h downregulates ABCG2 in pancreatic cancer cells to inhibit migration, invasion, and side populations" British Journal of Cancer (2010) 103, pp. 567-574.
Sarkar et al., "Implication of microRNAs in drug resistance for designing novel cancer therapy", Drug Resistance Updates, 13 (2010), pp. 57-66.
Yang et al., "Altered microRNA expression in cisplatin-resistant ovarian cancer cells and upregulation of miR-130a associated with MDR1/P-glycoprotein-mediated drug resistance", Oncology Reports, 28: 2012, pp. 592-600.
To et al., "Escape from hsa-miR-519c enables drug-resistance cells to maintain high expression of ABCG2", Mol Cancer Ther 2009; 8(10), Oct. 2009, pp. 2959-2968.
Boren et al., "MicroRNAs and their target messenger RNAs associated with ovarian cancer response to chemotherapy", Gynecologic Oncology, 113, 2009, pp. 249-255.
Wang et al., "hsa-miR-520h downregulates ABCG2 in pancreatic cancer cells to inhibit migration, invasion, and side populations", British Journal of Cancer, (2010) 103, pp. 567-574.

(Continued)

*Primary Examiner* — Dana Shin
(74) *Attorney, Agent, or Firm* — Norton Rose Fulbright US LLP

(57) ABSTRACT

The present invention concerns methods and compositions regarding one or more microRNAs or variants thereof that are provided to an individual for a variety of medical treatments, including sensitization to cancer therapy or prevention of a cancer to become sensitized to a cancer therapy. In specific embodiments, the microRNAs include miR-520a (including at least miR-520a-3p and miR-520-5p), miR-520g, miR-520h, and functional variants thereof. In some embodiments, the cancer is ovarian cancer, and in particular embodiments, the cancer therapy is platinum-based chemotherapy.

7 Claims, 12 Drawing Sheets

(56) References Cited

OTHER PUBLICATIONS

Su et al., "Downregulation of MicroRNA miR-520h by E14 Contributes to Anticancer Activity", Cancer Research, 70 :12), Jun. 15, 2010, pp. 5096-5108.
Zou et al., "MicroRNA-30a Sensitizes Tumor Cells to cis-Platinum via Supressing Beclin 1-mediated Autophagy", The Journal of Biological Chemistry vol. 287, No. 6, Feb. 3, 2012, pp. 4148-4156.
Zhang et at., "MicroRNA-520g Confers Drug Resistance by Regulating p21 Expression in Colorectal Cancer", The Journal of Biological Chemistry, vol. 290, No. 10, Mar. 6, 2015, pp. 6215-6225.
Boac et al.., Micro-RNAs associated with the evolution of ovarian cancer cisp resistance, Gynecologix Oncology, 140, (2016), pp. 259-263.
Database Geneseq [Online] Nov. 10, 2011, "Cell cycle regulation related microRNA (miRNA), SEQ ID 811.", retrieved from EBI accession No. GSN:AZM87987; Database accession No. AZM87987; & WO 2011/111715 A 1 (Kyowa Hakko Kirin Col To [JP]; Kinoshita Keit A [JP]; Yoshida Tetsuo [J) Sep. 15, 2011.
Database Geneseq [Online] Feb. 18, 2010, "Degranulation of mast cell related micro RNA precursor, SEQ ID 3822.", retrieved from EBI accession No. GSN:AXT86983; Database accession No. AXT86983; & WO 2009/148137 A 1 (Kyowa Hakko Kirin Co Ltd [JP]; Kosaka Kyoko; Yamada Yoji; Miura Kazumi) Dec. 10, 2009.
Ma et al: "Micro RNA and drug resistance", Cancer Gene Therapy, vol. 17, No. 8, Aug. 1, 2010, pp. 523-531.

\* cited by examiner

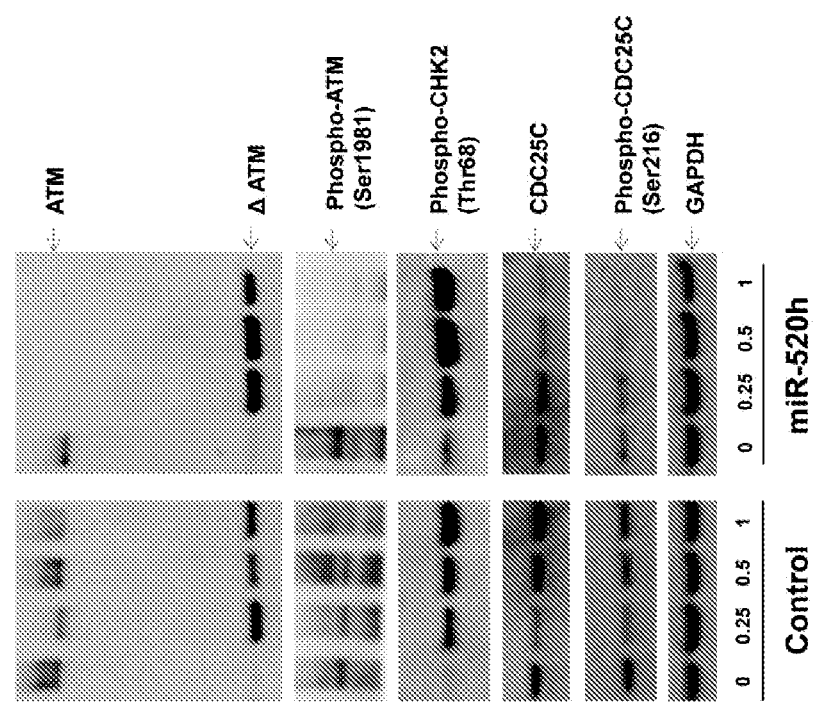
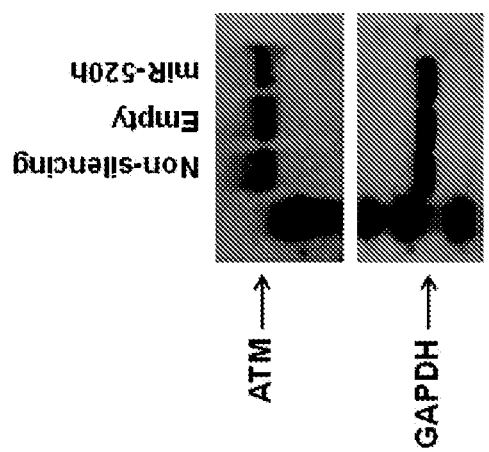
FIG. 8A-B

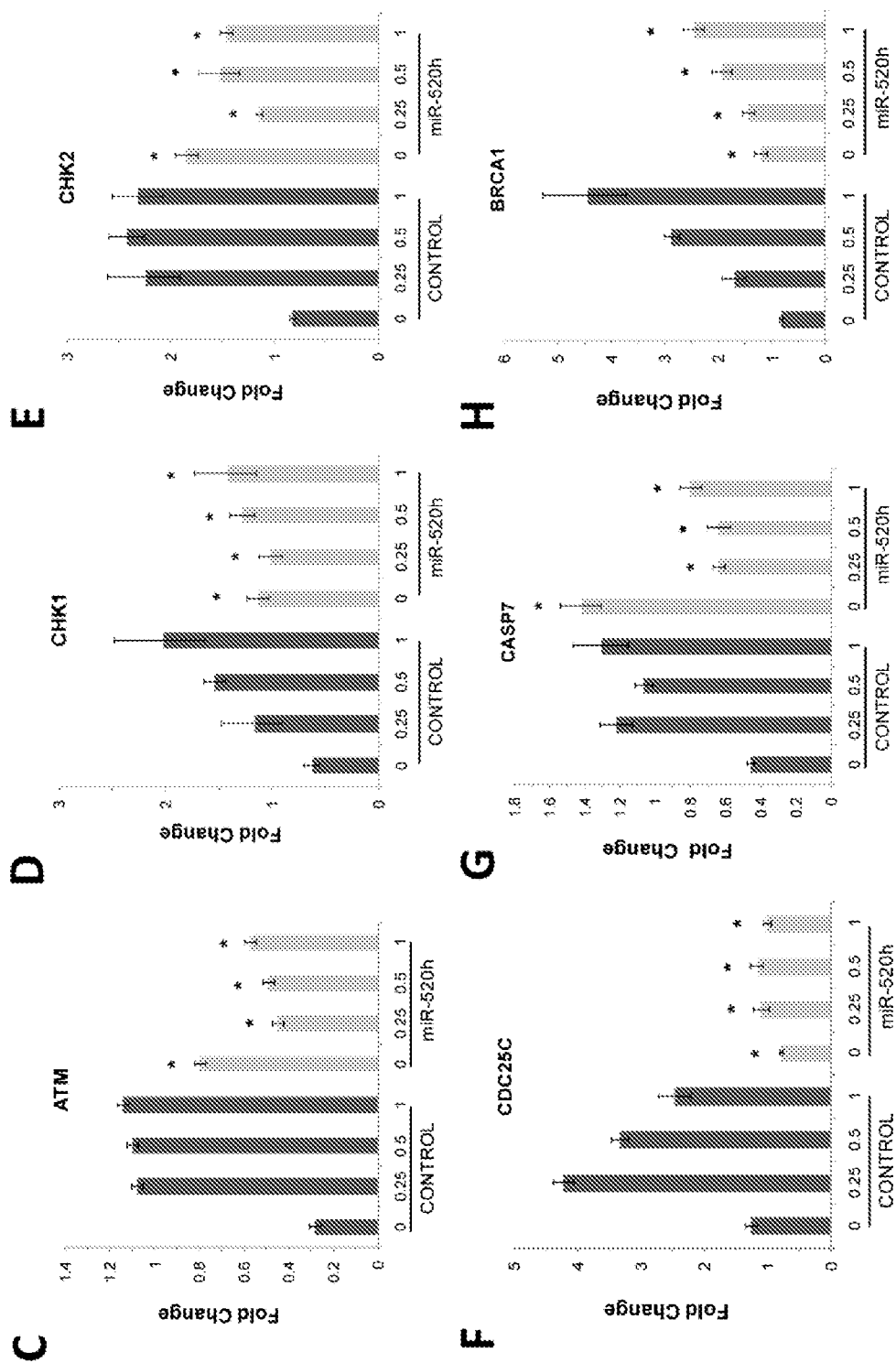
FIG. 8C-H

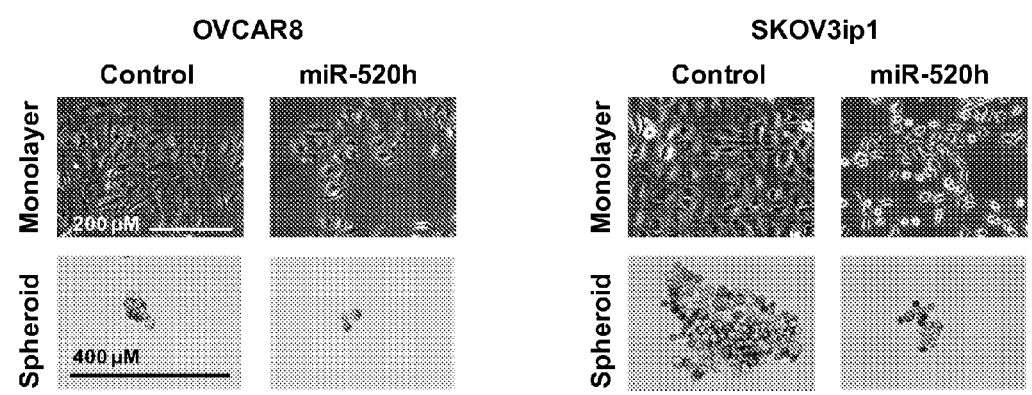
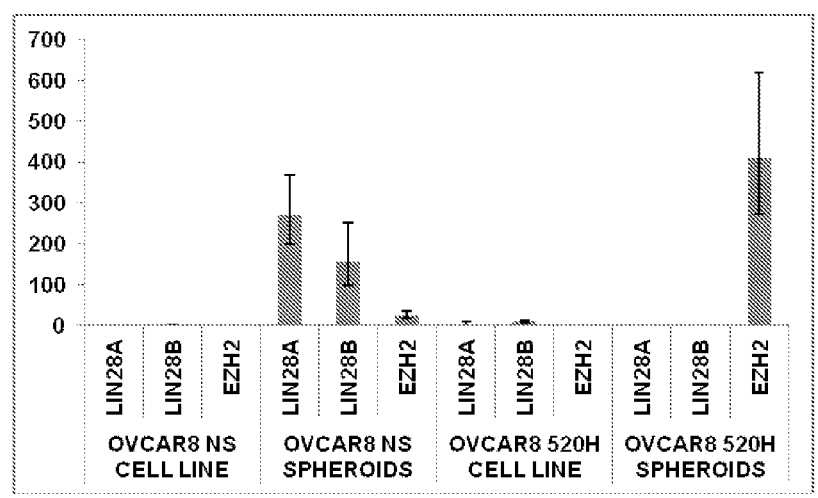
FIG. 9

SEQUENCE LISTING

```
<160> NUMBER OF SEQ ID NOS: 3

<210> SEQ ID NO 1
<211> LENGTH: 88
<212> TYPE: RNA
<213> ORGANISM: Homo sapiens

<400> SEQUENCE: 1
ucccaugcug ugacccucua gaggaagcac uuucuguuug uugucugaga aaaaacaaag      60
ugcuucccuu uagaguuacu guuuggga                                        88

<210> SEQ ID NO 2
<211> LENGTH: 90
<212> TYPE: RNA
<213> ORGANISM: Homo sapiens

<400> SEQUENCE: 2
ucccaugcug ugacccucua gaggaagcac uuucuguuug uugucugaga aaaaacaaag      60
ugcuucccuu uagaguguua ccguuuggga                                      90

<210> SEQ ID NO 3
<211> LENGTH: 85
<212> TYPE: RNA
<213> ORGANISM: Homo sapiens

<400> SEQUENCE: 3
cucaggcugu gacccuccag agggaaguac uuucuguugu cugagagaaa agaaagugcu      60
ucccuuugga cuguuucggu uugag                                           85
```

MIR-520 MICRORNAS SENSITIZE CANCERS TO PLATINUM-BASED THERAPY

This application is a national phase application under 35 U.S.C. §371 that claims priority to International Application No. PCT/US2013/050248 filed Jul. 12, 2013, which claims the benefit of priority to U.S. Provisional Patent Application Ser. No. 61/670,774, filed Jul. 12, 2012, and U.S. Provisional Patent Application Ser. No. 61/775,498, filed Mar. 9, 2013, all applications are incorporated herein by reference in their entirety.

TECHNICAL FIELD

The field of the invention concerns at least compositions and methods related to medical treatment, including at least treatment for cancer. In at least particular cases, the field of the invention concerns sensitization of one or more cancers to a particular treatment. In certain embodiments, the invention concerns at least cell biology and molecular biology.

BACKGROUND OF THE INVENTION

Recent evidence has implicated small RNA transcripts known as microRNAs in at least certain types of cancer. MicroRNAs (miRNAs) are small, non-coding RNA transcripts that play a critical role in silencing patterns of gene expression. The target specificity of individual microRNAs may be determined by a stretch of 6 nucleotides located from 2 through 7 of the mature microRNA transcript. These nucleotides, known as the "seed sequence" promote the binding of individual microRNAs to the 3' untranslated region of mRNA transcripts. The resulting duplex is incorporated into the RNA-induced silencing complex (RISC), leading to translational repression often as a result of mRNA degradation. Because sequences complementary to an individual microRNA seed can be found in many different 3'UTRs, a single microRNA can target hundreds of different mRNAs across and within multiple pathways.

One exemplary type of cancer in which miRNAs may play a role is ovarian cancer. Platinum-based chemotherapy is standard of care for all women newly diagnosed with an epithelial ovarian cancer. These drugs include carboplatin, cisplatin, oxaloplatin and may be used singly or in combination with other agents including paclitaxel, doxetaxel, gemcitabine, liposomal doxorubicin, bevacizumab, cyclophosphamide or topotecan. Despite excellent response rates (>80%), there are a number of issues associated with the use of platinum-based agents to treat ovarian cancer. First, not all ovarian cancers respond well to these treatments. Approximately 20% of women with advanced ovarian cancers demonstrate de novo resistance to these agents. Second, small (microscopic) volume disease persists after standard of care treatment even in those women who achieve a complete clinical response, as judged by imaging, serum levels of tumor marker and physical examination, for example. These implants eventually activate to repopulate disease recurrences. Third, recurrent ovarian cancer eventually becomes resistant to platinum-based therapy. Because platinum is currently by far the most effective agent used to treat ovarian cancer, nearly all women with recurrent disease are treated with platinum either alone or in combination with some other agent. However, with continued use, almost all ovarian cancers become resistant to its cytotoxic activity. Ultimately, nearly all (>90%) of women with ovarian cancer die from a platinum-resistant recurrence of their disease. Although higher doses of platinum agents have been shown to induce better responses, their use is limited because of the toxicity associated with dose escalation. Toxicities are also a problem for women being treated with current standard of care regimens. As many as 40% of women being treated for ovarian cancer with current regimens experience problems with severe neutropenia, neuropathy and/or kidney damage that require dose reductions, further limiting the ability of clinicians to utilize dose intense or dose escalation strategies for the treatment of ovarian and other human cancers with platinum agents. Other side effects that can require dose reductions that limit efficacy include neutropenia, anemia, renal dysfunction, poor appetite, myalgias, fatigue, nausea and vomiting. In situations where these side effects limit the use of platinum agents or where platinum agents are no longer effective, a number of phase II clinical trials have established the efficacy of agents that are used by clinicians to manage this disease. These agents include liposomal docetaxel, etoposide, gemcitabine, liposomal doxorubicin, topotecan, bevacizumab, altretamine capecitabine, cyclophosphamide, irinotecan, malphalan, oxaliplatin, pemetrexed and vinolrelbine. (1-7). The efficacy of each of these agents has been tested in phase II clinical trials that support their use in the context of platinum-resistant ovarian cancer. In addition to the dose regimens documented formally as part of phase II clinical trials, more recent data indicates that alternative dosing regimens of these agents alone or in combination may enhance the efficacy. For example, recent evidence suggests that the combination of paclitaxel administered on a weekly schedule in combination with bevacizumab administered every two weeks can induce response rates as high as 70% (8, 9). It should be noted that this combination was tested using a study group that include women with both platinum-sensitive and resistant ovarian cancer recurrences. Nonetheless, this observation is significant because response rates for most single agent regimens against platinum-resistant ovarian cancer range from 12-30% (1-7). Because nearly all agents used to treat ovarian cancer ultimately fall in their ability to arrest or reverse disease progression. Survival for women with platinum resistant ovarian cancer is 12-24 months.

The present invention addresses these issues and provides a solution for a long-felt need in the art to provide effective ovarian cancer treatment.

BRIEF SUMMARY OF THE INVENTION

The present invention is directed to methods and compositions related to treating or enhancing treatment of one or more medical conditions. The medical conditions may be of any kind, but in specific embodiments the medical conditions may be for hyperproliferative disease. In some embodiments the medical conditions encompass cancer of any kind, preeclampsia, placental dysfunction in pregnancy, conditions involving abnormal tissue differentiation such as colonic or endometrial polyps, preinvasive lesions such as cervical dysplasia and/or treating scars. In some cases, stem cells are targeted with compositions of the invention, and such targeting may be for any purpose including, at least, targeting to reduce or inhibit the ability to repopulate tumors in vivo and evade chemotherapy treatments.

In particular embodiments, the individual has been diagnosed with cancer and is in need of cancer treatment. The individual may or may not have one or more symptoms of cancer. The individual may be at risk for having cancer. The individual may be at risk for being resistant to one or more cancer treatments, and that risk may or may not have been recognized by a medical provider.

In particular embodiments there are methods and compositions for enhancement of cancer treatment, including at least chemotherapy, immunotherapy, radiation therapy, and/or hormone therapy, for example. In some embodiments, the methods and compositions concern the sensitization of cancer to one or more treatments. The cancer may have shown sensitization immediately upon treatment or the sensitization may have occurred after treatment had been provided for some time. In particular aspects, the sensitization to the treatment occurs directly or indirectly through administration of one or more microRNAs to an individual having received, receiving or who will be receiving cancer treatment. In specific embodiments, microRNAs 520 a, g, and/or h sensitize cancers to chemotherapy (including epithelial ovarian cancers, for example, to chemotherapy), immunotherapy, radiation therapy and/or hormone therapy.

In embodiments of the invention, one or more microRNAs of the invention are provided to an individual for sensitizing a cancer in the individual to a cancer treatment. In some embodiments, the individual is diagnosed as having cancer resistant to therapy and is in need of treating the cancer such that it becomes sensitive to one or more therapies to which it was previously resistant and is given the microRNA(s) with the explicit purpose of sensitizing the cancer. In specific aspects, the cancer treatment targets an entity (such as a gene or gene product) that is directly or indirectly affected by the microRNA of the invention. In some embodiments, the microRNA impacts cell cycle checkpoints, DNA damage repair pathways, and/or apoptosis, for example.

In some embodiments, microRNAs 520 a, g, and/or h prevent sensitization of one or more cancers before they become resistant to a therapy. In specific embodiments, microRNAs 520a, g, and/or h reverse acquired resistance to chemotherapy, including, for example, platinum, which typically occurs with time and can be because of genetic drift or selection of drug-resistant tumors with treatment, for example.

Although any treatment for any cancer may be affected by use of the microRNAs of the invention, in specific embodiments the cancer is ovarian cancer. The individual may have any type of ovarian cancer, including ovarian cancer types such as epithelial ovarian tumors (derived from the cells on the surface of the ovary); germ cell ovarian tumors (derived from the egg producing cells within the body of the ovary); and sex cord stromal ovarian tumors. The therapy for the ovarian cancer may be for treating any stage of ovarian cancer, including stage I, II, III, or IV. The ovarian cancer may have been diagnosed by physical exam, pelvic exam, blood tests, biopsy, and/or ultrasound, for example. The individual may have been asymptomatic or may have had symptoms such as pressure or pain in the abdomen, pelvis, back, or legs; a swollen or bloated abdomen; nausea, indigestion, gas, constipation, or diarrhea; and/or fatigue, for example. The ovarian cancer may or may not be metastatic at the time of treatment with the microRNAs of the invention. In specific embodiments the cancer treatment for which the cancer needs to be sensitized comprises platinum-based drugs, such as carboplatin or cisplatin, with a taxane such as paclitaxel (Taxol) or docetaxel (Taxotere). oxaliplatin, etoposide, ifosfamide, topotecan, gemcitabine, pegylated liposomal doxorubicin, doxorubicin, cyclophosphamide, epirubicin, altretamine irinotecan, pemetrexate, vinorelbine, tamoxifen, leuprolide, as well as other targeted biologic agents that have biologic activity against ovarian cancer. Examples of this latter category include bevacizumab, sunitinib and others.

In some embodiments, there is a method of sensitizing a cancer in an individual to a cancer treatment, comprising the step of administering to the individual an effective amount of a composition as follows: a) a RNA polynucleotide comprising SEQ ID NO:1, SEQ ID NO:2, or SEQ ID NO:3; or b) a RNA polynucleotide comprising sequence having one or more (for example, one, two, three, or more) nucleotide alterations in SEQ ID NO:1, SEQ ID NO:2, or SEQ ID NO:3, wherein upon administering the composition to the individual, the cancer is thereby sensitized to the treatment. In a specific embodiment, the composition is delivered to the individual by liposome, nanosphere, nanoparticle, nanodiamonds, impregnanted polymer, multistage nanoparticles and/or gels. In some cases, the composition is delivered to the individual intravenously or intraperitoneally. In specific embodiments, the cancer is ovarian cancer, uterine cancer, cervical cancer, lung cancer, colon cancer, breast cancer, or testicular cancer. In some aspects, the treatment is chemotherapy, immunotherapy, hormone therapy or a combination thereof. In particular cases, the treatment is platinum-based chemotherapy. In some embodiments, the method further comprises delivering the cancer treatment to the individual. The composition may be delivered to the individual prior to the cancer treatment or subsequent to the cancer treatment or concomitantly with the cancer treatment.

In some embodiments, there is an isolated composition, comprising an RNA polynucleotide having sequence comprising one or more (for example, one, two, three, or more) nucleotide alterations compared to SEQ ID NO:1, SEQ ID NO:2, or SEQ ID NO:3. In specific embodiments, the composition is comprised in a pharmaceutically acceptable carrier.

In particular embodiments, there is a recombinant polynucleotide comprising SEQ ID NO:1, SEQ ID NO:2, SEQ ID NO:3 or a functional variant thereof. In specific embodiments, the expression of SEQ ID NO:1, SEQ ID NO:2, or SEQ ID NO:3 is under the control of an inducible promoter, such as one selected from the group consisting of cytomegalovirus (CMV), Rous sarcoma virus (RSV), human serum albumin (SA), a-1 antitrypsin (AAT), cytochrome P450 CYP1A2, CYP2C9, CYP2C18, CYP2D6, CYP3A4, amyloid precursor protein (APP), nuclear factor j B (NFjB), and heat shock protein 70. In some cases, there is an isolated cell comprising a polynucleotide of the invention.

In some embodiments, there is a kit for treating cancer in an individual, said kit comprising in suitable container means: a) an RNA polynucleotide comprising SEQ ID NO:1, SEQ ID NO:2, or SEQ ID NO:3; and/or b) an RNA polynucleotide having sequence comprising one or more (for example, one, two, three, or more) nucleotide alterations compared to SEQ ID NO:1, SEQ ID NO:2, or SEQ ID NO:3. In specific embodiments, the method further comprises one or more cancer treatments, such as chemotherapy, immunotherapy, and/or hormone therapy. In specific cases, the chemotherapy comprises platinum-based chemotherapy.

Altered patterns of miRNA expression have now been documented in many different human diseases, including epithelial ovarian cancer (10-13). Recent evidence suggests that miRNA function may only become biologically evident under conditions of cellular stress (14, 15). In one aspect, the set of microRNAs involved in the pathogenesis of this disease may actually be distinct from those microRNAs capable of sensitizing formed tumors to current treatments. Because the majority of women ultimately succumb to ovarian cancer, the microRNAs that could potentially sensitize these tumors to drugs such as cisplatin must be either lost through deletion or remain repressed upon exposure to treatment. The inventors carried out a search for microRNAs that are predicted to target multiple genes regulating cell cycle checkpoints and DNA damage pathways that have been selectively repressed through copy losses in the genome. A unique, primate-specific genomic locus at 19q13.41 encoded more than 54 individual microRNAs. Although this genomic locus experiences frequent copy number variation in epithelial ovarian cancers, the microRNAs it encodes are only infrequently expressed in ovarian cancers. Nonetheless, these microRNAs are collectively predicted to target both the G1-S and G2/M checkpoints as well as multiple genes in the DNA damage pathways, such as ATM and ATR. On the basis of at least one or both of these two criteria, the inventors considered that microRNAs 520-a, g, and/or h are useful to sensitize epithelial ovarian cancers to established chemotherapies by altering the expression of a large number of oncogenes known to be critical for regulating genomic stability, proliferation and apoptosis. The results provide insight into the mechanisms by which microRNAs can be used to therapeutically target epithelial ovarian cancers and identify a novel mechanism by which ovarian cancer can be sensitized to cancer therapy, including at least platinum-based chemotherapy.

In certain aspects to the invention, medical conditions other than cancer may be treated with methods and/or compositions of the invention. In particular the medical conditions are those in which administration of microRNAs 520-a, g, and/or h are therapeutic. One particular example of such a medical condition includes at least preeclampsia. An individual that has preeclampsia or is suspected of having preeclampsia (symptoms include hypertension, proteinuria, and/or swelling) may be provided with methods and/or compositions of the invention and, in some cases, they are given one or more other therapies, or Caesarean section or induction of labor (and therefore delivery of the placenta) may occur. The individual may have preeclampsia for any reason or at any stage during the pregnancy.

Another example of a medical condition in which administration of microRNAs 520-a, g, and/or h is therapeutic includes placental dysfunction in pregnancy. The dysfunction may be of any kind. In some cases, the placental dysfunction is placental insufficiency, which includes insufficient blood flow to the placenta and during pregnancy. Placental insufficiency includes symptoms such as amnion cell metaplasia and placental thickness less than 1 cm, for example. It can also be reflected in impaired transplacental transport of nutrients. The individual being treated may be known to have placental dysfunction or may be suspected of having placental dysfunction, and other treatments may be given to the individual, such as bedrest, induction of labor, or Caesarean section.

An additional example of a medical condition in which administration of microRNAs 520-a, g, and/or h is therapeutic includes treating scars. The scar may be of any kind, including external or internal, and the cause of the scar may be of any kind. The scar may be anywhere on or in the body and may be new or old and includes categories of hypertrophic scars known as keloids. This includes the formation or prevention of intraperitoneal adhesions. In specific embodiments, the methods and/or compositions of the invention are provided to the scar after its formation or are alternatively or in addition provided to a wound site before scar formation. Any type of scar may be treated including keloid scars, contracture scars, hypertrophic scars, and/or acne scars. The composition of the invention may be provided to the individual locally or systemically. The composition of the invention may be provided to the individual with another therapeutic composition for scar treatment and/or prevention (such as silicone or onion extract, for example).

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 8. Mir-520g/h expression silences the response of apoptosis and DNA damage repair pathways activated by cisplatin exposure. (A) Expression of the tumor suppressor ATM is markedly reduced in OVCAR8 cells stably expressing miR-520 when compared to clones stably transfected with either non-silencing control or empty vector. (B). MiR-520h promotes a proteolytic degradation of ATM that normally occurs in response to cisplatin. This is evidenced by increased more robust expression of cleaved ATM dimers, the smaller protein product (ΔATM) recognized by the ATM antibody (see labeled arrow, B). Increased ATM degradation is associated with decreased levels of ATM and phosphoATM. Consistent with increased levels of ATM activity, increased levels of phopho-CHK2 (T68) are observed in the presence of miR-520h. In addition, expression of miR-520h blunts the responses of multiple gene products to cisplatin. These gene products include CHK1 (D), CHK2 (E), CDC25C (F), CASP7 (G) and BRCA1 (H). Note that the impact of increased ATM activity does not uniformly impact all ATM-regulated pathways, as decreased levels of CDC25c and phospho-CDC25c protein are found in OVCAR8 cells (B), likely as a result of miR-520g/h-induced translational silencing of its upstream regulator CHK1 when OVCAR8 cells are incubated with cisplatin (D). All qPCR results marked by an asterisk (*) significant with $p<0.05$. Error bars reflect standard deviation calculated from 5 biologic replicates.

FIG. 9: Mimics for miR-520g/h impact creation of spheroids, a key intermediate in metastasis and cancer stem cells and impact patterns of cancer stemness. OVCAR8 and SVOK3ip1 cells stably expressing mimics for miR-520h demonstrate decreased capacity to form spheroids, multicellular aggregates that play a key role in ovarian cancer metastasis. (A) Spheroids have also been used to isolate subpopulations of cells that fulfill many of the criteria of cancer stem cells and express enhanced levels of specific gene products including EZH2, OCT4 and NANOG associated with pleuripotency in human embryonic stem cells (16). (B) Expression of miR-520gh impacts patterns of and eliminates increased expression of specific patterns of gene expression (i.e. lin28A/B) associated with stemness that are induced when ovarian cancer cells (OVCAR8 and SKOV3ip1) are cultured in media that induce spheroid formation.

DETAILED DESCRIPTION OF THE INVENTION

Figure 1:
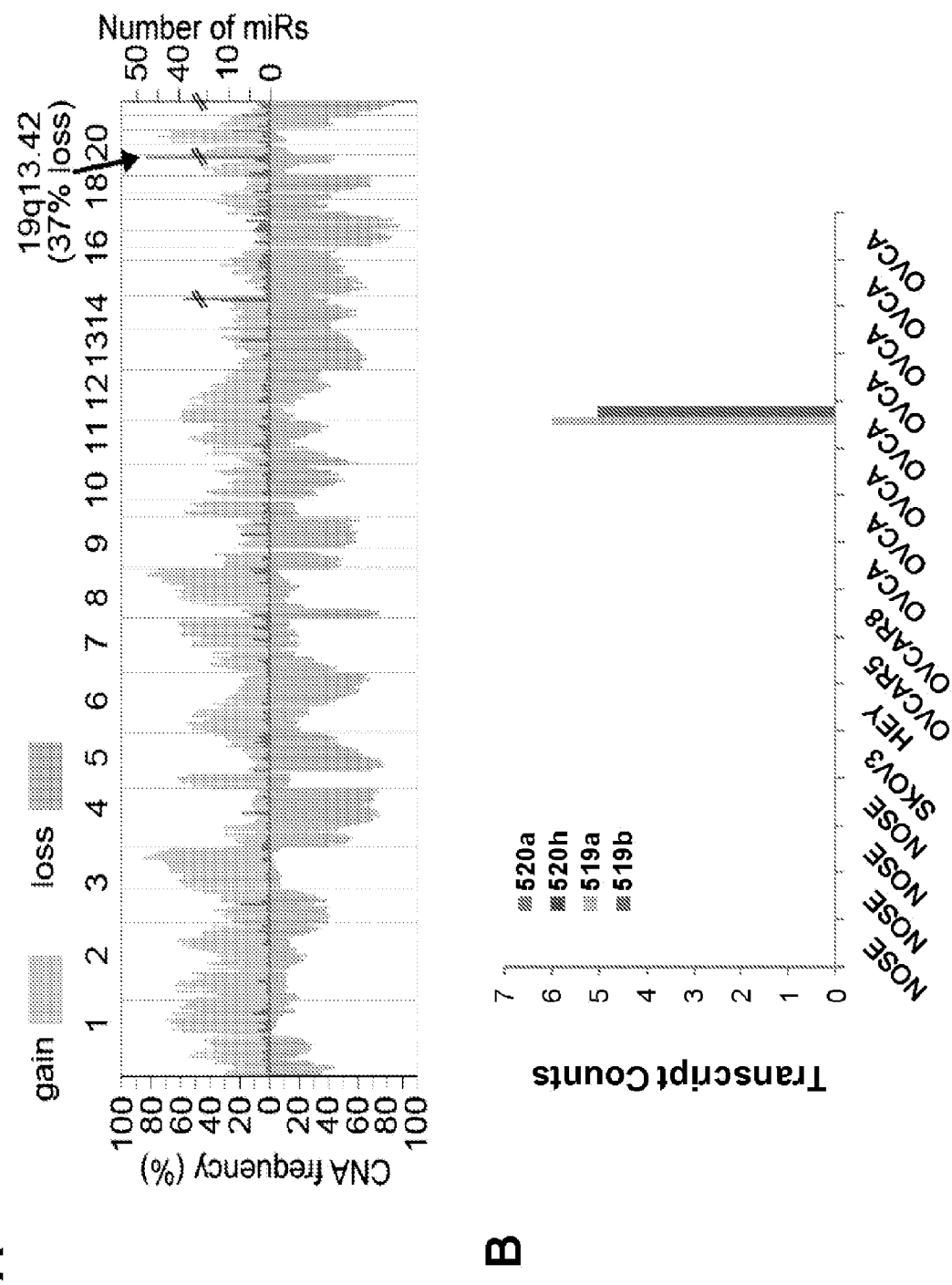
FIG. 1: Genomic copy number variation and microRNA expression in epithelial ovarian cancers. (A) Copy number gains (yellow) and losses (blue) identified in a 500 specimens of high grade serous ovarian cancers are plotted as a function of chromosome location. Location of known human microRNAs (mirBase v.16) are identified in gray. Note that copy number gains and losses at 19q13.41, the site of miR-520g/h occur frequently in EOC at a unique genomic locus encoding more than 45 mature human microRNAs. (B) Expression of specific microRNAs in specimens of fallopian tube, short term primary culture of ovarian surface epithelia and epithelial ovarian cancers evaluated by Next Generation Sequencing of cloned small RNA libraries. Note that very few small RNA transcripts could be detected in any of the specimens studied that correspond to miR-520a, miR-520g/h. (C) Outcome demographics indicate that survival is significantly improved when subset of ovarian cancer patients with highest expression of miR-520g/h are compared to 340 patients with lowest levels of miR-520g/h expression.
Figure 1C:
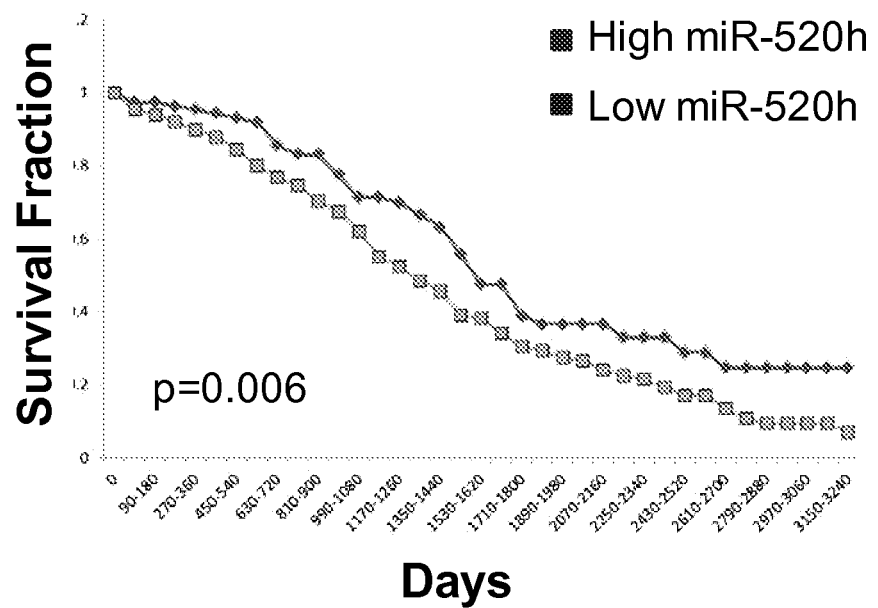

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein. Embodiments discussed in the context of methods and/or compositions of the invention may be employed with respect to any other method or composition described herein. Thus, an embodiment pertaining to one method or composition may be applied to other methods and compositions of the invention as well.

Throughout this application, the term "about" is used to indicate that a value includes the standard deviation of error for the device or method being employed to determine the value.

The term "sensitizes" as used herein refers to one or more agents that promote the efficacy or improve function of a cancer treatment.

I. General Embodiments of the Invention

Using a dataset of gene and micro/RNA expression generated from nearly 500 high grade epithelial ovarian cancers, the inventors identified a unique genomic locus at 19q13.41 that encodes more than 45 individual microRNAs. Using Kaplan-Meier survival analyses, the inventors found that levels for microRNAs 520-a, g, and/or h encoded by this locus correlate with outcomes for women with ovarian cancer. In certain embodiments, the data indicate that mimics for at least one of these microRNAs (miR-520h, for example) can be used to dramatically sensitize established ovarian cancer cell lines to cisplatin both in vitro and in vivo. The $IC_{50}$ for cisplatin in multiple ovarian cancer cell lines is reduced as much as 4-fold in OVCAR8 and SKOV3ip1 cells ($p<0.001$). At a molecular level and in certain embodiments, miR-520h accomplishes this feat by targeting multiple gene products previously implicated in platinum responses. These include key components of DNA damage repair pathways (ATM), gene products regulating the G1-S and G2-M cell cycle checkpoints, apoptosis and cell migration. Most dramatically, the representative miR-520h improves survival of mice xenografted with ovarian cancer when treated with very low dose cisplatin at less than 5% of those currently used to clinically manage ovarian cancer in women. Mean survival for mice receiving miR-520h, for example, is 130 days compared to when mice are treated with a biweekly maintenance IV regimen of 5 mg/m$^2$ cisplatin (compared to 50-100 mg/m$^2$ typically used to achieve therapeutic responses.) These data provide dramatic and convincing evidence that miR-520h can be used to sensitize ovarian cancer to platinum-based chemotherapy and improve survival. Other microRNAs from 19q13.41 may be similarly used.

Treatment with one or more microRNAs of the present invention can be incorporated into frontline therapy for newly diagnosed epithelial ovarian cancer (EOC). Given the widespread use of platinum-based agents to treat other human cancers, a role for microRNA (including miR-520-a, g, and/or h: 5'-caaagug is the seed for miR-520g/h; the seed for miR-520a is 5'aagugcu) treatments can also be reasonably anticipated in at least angiosarcomas, lung cancer, cervical cancer, colon cancer, bladder cancer, testicular cancer, head and neck cancers, and so forth. Use of one or more microRNAs of the invention (including miR-520-a, g, and/or h) will improve outcomes for individuals diagnosed with a wide-range of malignancies.

The compositions of the invention are unique in that they target multiple gene products across different signaling pathways involved in platinum resistance. The fact that response to platinum chemotherapy is determined by multiple gene products is an aspect that has thwarted the effective clinical development of agents for this purpose.

In embodiments of the invention, one can demonstrate in vivo safety and efficacy of liposomal miR-520h nanoparticles using xenograft models of ovarian cancer. In embodiments of the invention, one can determine the ideal route, timing and dosage for miR-520h liposomes necessary to achieve optimal tumor shrinkage. In embodiments of the invention, one can demonstrate that miR-520h liposomes administered at an optimal timing and dose given with combination platinum-based chemotherapy at reduced dosage improve outcomes even when compared to combination platinum-based chemotherapy at standard doses.

In specific embodiments, the microRNA treatments are delivered in infusion centers, clinics and hospital where ovarian cancer patients currently receive care.

In certain aspects of the invention, one or more microRNAs are employed to sensitize cancer to platinum-based chemotherapy agents that work by cross-linking subunits of DNA. These agents act during all parts of the cell cycle and impair DNA synthesis, transcription, and function. First generation platinum-based chemotherapeutics include cisplatin, although it is highly toxic and can severely damage the kidneys. The second generation platinum-complex carboplatin (cis-diammine-[1,1-cyclobutanedicarboxylato] platinum(II)) much less toxic in comparison and have fewer kidney-related side effects. Oxaliplatin, which is third generation platinum-based complex, is used to treat colon cancer, for example.

In certain embodiments of the invention, microRNAs miR-520-a, g, and/or h dramatically sensitize ovarian cancers to platinum-based chemotherapy. Synthetic mimics for miR-520h, for example, can be safely delivered to women with ovarian cancer and used to increase the potency of platinum-based agents, while reducing the incidence of side effects and dramatically improving outcomes. The inventors envision the use of liposomes containing miR-520h mimics (or those for mir-520a or g) that can be delivered either intraperitoneally or intravenously as part of treatments for ovarian cancer in a number of clinical contexts. The reagents used to synthesize these liposomes can allow for the cost effective, readily scalable mass production of a clinical vector that can be incorporated into standard of care treatments for ovarian cancer. Given the central role that platinum-based agents play in standard of care treatment for other human cancers, the present invention is useful and effective for treating a wide range of other cancers.

II. Exemplary MicroRNAs of the Invention

In embodiments of the invention, microRNAs miRNA 520 a, g, and/or h are provided to an individual for cancer treatment. In particular embodiments, one or more microRNAs are provided to an individual to improve the efficacy of a treatment. The cancer treatment may be of any kind, but in specific cases the treatment is chemotherapy, radiation therapy, hormone therapy, or immunotherapy or targeted therapy directed at specific subsets of cancer cancers, including cancer stem cells (CDCs) or cancer initiating cells (CICs), vascular cells, or stroma. In certain aspects, the anti-cancer treatment is platinum-based chemotherapy.

The term "miRNA" is used according to its ordinary and plain meaning and refers to a microRNA molecule found in eukaryotes that is involved in RNA-based gene regulation. See, e.g., Carrington et al., 2003, which is hereby incorporated by reference. The term may be used to refer to the RNA molecule processed from a precursor.

In certain aspects, the one or more microRNAs is selected from the group consisting of miR-520a (including at least miR-520a-3p and miR-520-5p), miR-520g, miR-520h, and functional variants thereof.

```
hsa-mir-520h MI0003175:
                                          (SEQ ID NO: 1)
UCCCAUGCUGUGACCCUCUAGAGGAAGCACUUUCUGUUUGUUGUCUGAG
AAAAAACAAAGUGCUUCCCUUUAGAGUUACUGUUUGGGA hsa-mir-520g MI0003166:
                                          (SEQ ID NO: 2)
UCCCAUGCUGUGACCCUCUAGAGGAAGCACUUUCUGUUUGUUGUCUGAG
AAAAAACAAAGUGCUUCCCUUUAGAGUGUUACCGUUUGGGA hsa-mir-520a MI0003149
                                          (SEQ ID NO: 3)
CUCAGGCUGUGACCCUCCAGAGGGAAGUACUUUCUGUUGUCUGAGAGAA
AAGAAAGUGCUUCCCUUUGGACUGUUUCGGUUUGAG
```

It is well known in the art that modifications can be made to the sequence of a miRNA or a pre-miRNA without disrupting miRNA activity, including miR-520a (including at least miR-520a-3p and miR-520-5p), miR-520g, miR-520h, and functional variants thereof. As used herein, the term "functional variant" of a miRNA sequence refers to an oligonucleotide sequence that varies from the natural miRNA sequence, but retains one or more functional characteristics of the miRNA (e.g. enhancement of cancer cell susceptibility to chemotherapeutic agents, cancer cell proliferation inhibition, induction of cancer cell apoptosis, specific miRNA target inhibition). In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant may be capable of hybridizing to one or more target sequences of the miRNA. Also encompassed in the invention is the use of oligonucleotides of any length that are processed into mature miRNAs, including miR-520a (including at least miR-520a-3p and miR-520-5p), miR-520g, miR-520h, and functional variants thereof. A functional variant may comprise one, two, three, four, five, six, seven, eight, or more alterations compared to a particular miRNA or precursor thereof.

In some embodiments, the complementary strand is modified so that a chemical group other than a phosphate or hydroxyl is at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin.

In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

In some embodiments, miRNA sequences of the invention may be associated with a second RNA sequence that may be located on the same RNA molecule or on a separate RNA molecule as the miRNA sequence. In such cases, the miRNA sequence may be referred to as the active strand, while the encoded RNA sequence, which is at least partially complementary to the miRNA sequence, may be referred to as the complementary strand. The active and complementary strands may be hybridized to generate a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand, for example.

miRNA used in the reaction may be obtained by a variety of methods and from a variety of sources. The miRNA may be obtained from a biological sample, such as a cell, tissue, or organ. It may be isolated from a biological sample that contains other RNA molecules as well, such as mRNA, tRNA, and/or rRNA. In certain instances, total RNA is first isolated from the sample and then the miRNA is separated from the other RNA, thereby enriching for miRNA. In some embodiments, the miRNA has been isolated away from other RNA to enrich for the miRNA, such that the miRNA substantially pure, meaning it is at least about 80%, 85%, 90%, 95% pure or more, but less than 100% pure, with respect to other RNA molecules. Alternatively, enrichment of miRNA may be expressed in terms of fold enrichment. In certain embodiments, miRNA is enriched by about, at least about, or at most about 5×, 10×, 20×, 30×, 40×, 50×, 60×, 70×, 80×, 90×, 100×, 250×, 500×, 1000×, and so forth. In some embodiments, the miRNA polynucleotide is synthesized.

MicroRNA molecules ("miRNAs") are generally 21 to 22 nucleotides in length, though lengths of 19 and up to 23 nucleotides have been reported. The miRNAs are each processed from a longer precursor RNA molecule ("precursor miRNA"). Precursor miRNAs are transcribed from non-protein-encoding genes. The precursor miRNAs have two regions of complementarity that enables them to form a stem-loop- or fold-back-like structure, which is cleaved by an enzyme called Dicer in animals. Dicer is ribonuclease III-like nuclease. The processed miRNA is typically a portion of the stem.

The processed miRNA (also referred to as "mature miRNA") become part of a large complex to down-regulate a particular target gene or genes. Examples of animal miRNAs include those that imperfectly basepair with the target, which halts translation (Olsen et al, 1999; Seggerson et al, 2002)

In some embodiments of the invention, there is an isolated composition, comprising SEQ ID NO:1, SEQ ID NO:2, or SEQ ID NO:3, respectively, wherein certain nucleotides therein are non-variable and/or one or more (including 1, 2, 3, 4, 5, 6, 7, 8, 9, or more) of the remaining nucleotides in the sequence are variable compared to SEQ ID NO:1, SEQ ID NO:2, or SEQ ID NO:3, respectively, wherein the composition has activity of sensitizing cancer to a therapy.

In specific aspects, variants of the miRNA sequence are employed. In certain embodiments, the seed sequence (which, for example, is shared between miR-520h and miR-520g) is not varied in the variants of the respective miRNA sequence. In other aspects, the anchor sequence is not varied in the variants of the respective miRNA sequence.

III. Inhibitors of miRNAs

In some embodiments of the invention, one or more inhibitors of miR-520a (including at least miR-520a-3p and miR-520-5p), miR-520g, miR-520h, and functional variants thereof, and/or methods of using them are encompassed in the invention. Methods of using inhibitors of miR-520 a, g, and/or h include those for treating an individual in need thereof. In certain embodiments, the inhibitors of miR-520 a, g, and/or h are employed in medical conditions in which there is an increased level of miR-520 a, g, and/or h compared to the levels in a normal standard. The medical condition may be of any kind having such elevated levels, but in specific embodiments the medical condition is angiosarcomas, conditions that rely on dysregulated pluripotency (i.e. stems cells).

The inhibitors of miR-520 a, g, and/or h encompassed in the invention may be of any kind, but in specific embodiments the inhibitors comprise at least nucleic acid, protein, and/or small molecules. In specific embodiments the inhibitors are nucleic acid that have sequence that is complementary to at least part of a miR-520 a, g, and/or h. In particular embodiments the inhibitor is an antisense inhibitor. In at least some cases, the inhibitor is specific for the respective miR-520 a, g, and/or h. Design of the nucleic acid inhibitor takes into consideration AT-rich microRNA targets, if applicable. Commercial products and assays for using them are available to the skilled artisan (for example, Exiqon, Woburn, Mass.; and Life Technologies TaqMan® MicroRNA Assays; ThermoScientific, Waltham, Mass.).

IV. Nucleic Acids

The present invention concerns miRNAs that can be used in therapeutic applications. The RNA may have been endogenously produced by a cell, or been synthesized or produced chemically or recombinantly. They may be isolated and/or purified. The term "miRNA," unless otherwise indicated, refers to the processed RNA, after it has been cleaved from its precursor.

Nucleic acids of the invention may have regions of identity or complementarity to another nucleic acid. It is contemplated that the region of complementarity or identity can be at least 5 contiguous residues, though it is specifically contemplated that the region is, is at least, or is at most 6, 7, 8, 9, 10, 11, 12, 13, 14, 15, 16, 17, 18, 19, 20, 21, 22, 23, 24, 25, or more contiguous nucleotides, where appropriate. It is further understood that the length of complementarity between an miRNA and its target gene(s) are such lengths. Moreover, the complementarity may be expressed as a percentage, meaning that the complementarity between a miRNA and its target is 80% or greater over the length of the miRNA or a noted fragment thereof. On some embodiments, complementarity is or is at least 80%, 85%, 90%, 91%, 92%, 95%, 97%, 99%, or 100%, for example.

It is understood that an miRNA can be derived from genomic sequences or a gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The term "recombinant" may be used and this generally refers to a molecule that has been manipulated in vitro or that is the replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mKNA transcript or a nucleic acid segment thereof, and the like.

Stringent conditions may comprise low salt and/or high temperature conditions, such as provided by about 0.02 M to about 0.5 M NaCl at temperatures of about 42° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

A. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA) and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, carboxyalkyl, amino, hydroxyl, halogen (i.e., fluoro, chloro, bromo, or iodo), thiol or alkylthiol moiety. Preferred alkyl (e.g., alkyl, carboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N5N-diemethyladenine, an azaadenines, a 8-bromoadenine, a 8-hydroxyadenine, a 6-hydroxyaminopurine, a 6-thiopurine, a 4-(6-aminohexyl/cytosine)5 and the like. Other examples are well known to those of skill in the art.

A nucleobase may be comprised in a nucleoside or nucleotide, using any chemical or natural synthesis method described herein or known to one of ordinary skill in the art. Such nucleobase may be labeled or it may be part of a molecule that is labeled and contains the nucleobase.

B. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

C. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar.

The attachment of the backbone moiety typically occurs at either the 3'- or 5'-position of the 5-carbon sugar However, other types of attachments are known in the art, particularly when a nucleotide comprises derivatives or analogs of a naturally occurring 5-carbon sugar or phosphorus moiety.

D. Nucleic Acid Analogs

A nucleic acid may comprise, or be composed entirely of, a derivative or analog of a nucleobase, a nucleobase linker moiety and/or backbone moiety that may be present m a naturally occurring nucleic acid. RNA with nucleic acid analogs may also be labeled according to methods of the invention As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in U.S. Pat. No. 5,681,947, which describes oligonucleotides comprising purine derivatives that form triple helixes with and/or prevent expression of dsDNA; U.S. Pat. Nos. 5,652,099 and 5,763,167, which describe nucleic acids incorporating fluorescent analogs of nucleosides found m DNA or RNA, particularly for use as fluorescent nucleic acids probes; U.S. Pat. No. 5,614,617, which describes oligonucleotide analogs with substitutions on pyrimidine rings that possess enhanced nuclease stability, U.S. Pat. Nos. 5,670,663, 5,872,232 and 5,859,221, which describe oligonucleotide analogs with modified 5-carbon sugars (i.e., modified 2'-deoxyfuranosyl moieties) used in nucleic acid detection; U.S. Pat. No. 5,446,137, which describes oligonucleotides comprising at least one 5-carbon sugar moiety substituted at the 4' position with a substituent other than hydrogen that can be used in hybridization assays, U.S. Pat. No. 5,886,165, which describes oligonucleotides with both deoxyribonucleotides with 3'-5' internucleotide linkages and ribonucleotides with 2'-5' internucleotide linkages, U.S. Pat. No. 5,714,606, which describes a modified internucleotide linkage wherein a 3'-position oxygen of the internucleotide linkage is replaced by a carbon to enhance the nuclease resistance of nucleic acids; U.S. Pat. No. 5,672,697, which describes oligonucleotides containing one or more 5' methylene phosphonate internucleotide linkages that enhance nuclease resistance, U.S. Pat. Nos. 5,466,786 and 5,792,847, which describe the linkage of a substituent moiety which may comprise a drug or label to the 2' carbon of an oligonucleotide to provide enhanced nuclease stability and ability to deliver drugs or detection moieties, U.S. Pat. No. 5,223,618, which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA, U.S. Pat. No. 5,470,967, which describes oligonucleotides composing at least one sulfamate or sulfamide internucleotide linkage that are useful as nucleic acid hybridization probe; U.S. Pat. Nos. 5,378,825, 5,777,092, 5,623,070, 5,610,289 and 5,602,240, which describe oligonucleotides with three or four atom linker moiety replacing phosphodiester backbone moiety used for improved nuclease resistance, cellular uptake and regulating RNA expression, U.S. Pat. No. 5,858,988, which describes hydrophobic carrier agent attached to the 2'-O position of oligonucleotides to enhanced their membrane permeability and stability; U.S. Pat. No. 5,214,136, which describes oligonucleotides conjugated to anthraquinone at the 5' terminus that possess enhanced hybridization to DNA or RNA, enhanced stability to nucleases, U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H, and U.S. Pat. No. 5,708,154, which describes RNA linked to a DNA to form a DNA-RNA hybrid, U.S. Pat. No. 5,728,525, which describes the labeling of nucleoside analogs with a universal fluorescent label.

Additional teachings for nucleoside analogs and nucleic acid analogs are U.S. Pat. No. 5,728,525, which describes nucleoside analogs that are end-labeled, U.S. Pat. Nos. 5,637,683, 6,251,666 (L-nucleotide substitutions), and U.S. Pat. No. 5,480,980 (7-deaza-2'deoxyguanosine nucleotides and nucleic acid analogs thereof).

E. Modified Nucleotides

Labeling methods and kits of the invention specifically contemplate the use of nucleotides that are both modified for attachment of a label and can be incorporated into an miRNA molecule Such nucleotides include those that can be labeled with a dye, including a fluorescent dye, or with a molecule such as biotin. Labeled nucleotides are readily available; they can be acquired commercially or they can be synthesized by reactions known to those of skill in the art.

Modified nucleotides for use in the invention are not naturally occurring nucleotides, but instead, refer to prepared nucleotides that have a reactive moiety on them. Specific reactive functionalities of interest include: ammo, sulfhydryl, sulfoxyl, ammosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, lodoacetyl, cyanomethyl ester, p-nitrophenyl ester, o-nitrophenyl ester, hydroxypyridine ester, carbonyl imidazole, and the other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the miRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in many embodiments are alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors, e.g., Sigma, Roche, Ambion, and NEN. Functional groups may be prepared according to ways known to those of skill in the art, including the representative information found in U.S. Pat. Nos. 4,404,289; 4,405,711; 4,337,063, 5,268,486 and Br. Pat. No. 1,529,202, which are all incorporated by reference.

Amine-modified nucleotides are used in several embodiments of the invention. The amine-modified nucleotide is a nucleotide that has a reactive amine group for attachment of the label. It is contemplated that any ribonucleotide (G, A, U, or C) or deoxyribonucleotide (G,A,T, or C) can be modified for labeling. Examples include, but are not limited to, the following modified ribo- and deoxyribo-nucleotides: 5-(3-aminoalryl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; N6-(4-amino) butyl-dATP, N6-(6-amino)butyl-dATP, N6-(6-Amino)hexyl-dATP; 8-[(6-Amino)hexyl]-amino-dATP; 5-propargylamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

F. Preparation of Nucleic Acids

A nucleic acid may be made by any technique known to one of ordinary skill in the art, such as for example, chemical synthesis, enzymatic production or biological production. In some embodiments, miRNA compositions of the invention are chemically synthesized.

In some embodiments of the invention, miRNAs are recovered from a biological sample. The miRNA may be recombinant or it may be natural or endogenous to the cell (produced from the cell's genome). It is contemplated that a biological sample may be treated in a way so as to enhance the recovery of small RNA molecules such as miRNA. U.S. patent application Ser. No. 10/667,126 describes such methods and it is specifically incorporated by reference herein. Generally, methods involve lysing cells with a solution having guanidinium and a detergent.

Alternatively, nucleic acid synthesis is performed according to standard methods. See, for example, Itakura and Riggs (1980). Additionally, U.S. Pat. No. 4,704,362, U.S. Pat. No. 5,221,619, and U.S. Pat. No. 5,583,013 each describe various methods of preparing synthetic nucleic acids. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al, 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 1989, incorporated herein by reference).

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Basically, chemical synthesis can be achieved by the diester method, the triester method polynucleotides phosphorylase method and by solid-phase chemistry. These methods are discussed in further detail below.

Diester Method.

The diester method was the first to be developed to a usable state, primarily by Khorana and co-workers. (Khorana, 1979). The basic step is the joining of two suitably protected deoxynucleotides to form a dideoxynucleotide containing a phosphodiester bond. The diester method is well established and has been used to synthesize DNA molecules (Khorana, 1979).

Triester Method.

The main difference between the diester and triester methods is the presence, in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore purification's are done in chloroform solutions. Other improvements in the method include (i) the block coupling of trimers. and larger oligomers, (ii) the extensive use of high-performance liquid chromatography for the purification of both intermediate and final products, and (iii) solid-phase synthesis.

Polynucleotide Phosphorylase Method.

This is an enzymatic method of DNA synthesis that can be used to synthesize many useful oligonucleotides (Gillam et al., 1978; Gillam et al., 1979). Under controlled conditions, polynucleotide phosphorylase adds predominantly a single nucleotide to a short oligonucleotide. Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-Phase Methods.

drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers.

Phosphoramidite chemistry (Beaucage and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

Recombinant Methods.

Recombinant methods for producing nucleic acids in a cell are well known to those of skill in the art. These include the use of vectors (viral and non-viral), plasmids, cosmids, and other vehicles for delivering a nucleic acid to a cell, which may be the target cell or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference.

In certain embodiments, the present invention concerns nucleic acid molecules that are not synthetic. In some embodiments, the nucleic acid molecule has a chemical structure of a naturally occurring nucleic acid and a sequence of a naturally occurring nucleic acid, such as the exact and entire sequence of a single stranded primary miRNA (see Lee 2002), a single-stranded precursor miRNA, or a single-stranded mature miRNA. In addition to the use of recombinant technology, such non-synthetic nucleic acids may be generated chemically, such as by employing technology used for creating oligonucleotides.

G. Isolation of Nucleic Acids

Nucleic acids may be isolated using techniques well known to those of skill in the art, though in particular embodiments, methods for isolating small nucleic acid molecules and/or isolating RNA molecules can be employed. Chromatography is a process often used to separate or isolate nucleic acids from protein or from other nucleic acids. Such methods can involve electrophoresis with a gel matrix, filter columns, alcohol precipitation, and/or other chromatography. If miRNA from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

In particular methods for separating miRNA from other nucleic acids, a gel matrix is prepared using polyacrylamide, though agarose can also be used. The gels may be graded by concentration or they may be uniform. Plates or tubing can be used to hold the gel matrix for electrophoresis. Usually one-dimensional electrophoresis is employed for the separation of nucleic acids. Plates are used to prepare a slab gel, while the tubing (glass or rubber, typically) can be used to prepare a tube gel. The phrase "tube electrophoresis" refers to the use of a tube or tubing, instead of plates, to form the gel. Materials for implementing tube electrophoresis can be readily prepared by a person of skill in the art or purchased, such as from C.B.S. Scientific Co., Inc. or Scie-Plas.

Methods may involve the use of organic solvents and/or alcohol to isolate nucleic acids, particularly miRNA used in methods and compositions of the invention. Some embodiments are described in U.S. patent application Ser. No. 10/667,126, which is hereby incorporated by reference. In specific embodiments, miRNA isolation processes include: a) lysing cells in the sample with a lysing solution comprising guanidinium, wherein a lysate with a concentration of at least about 1 M guanidinium is produced; b) extracting miRNA molecules from the lysate with an extraction solution comprising phenol; c) adding to the lysate an alcohol solution for form a lysate/alcohol mixture, wherein the concentration of alcohol in the mixture is between about 35% to about 70%; d) applying the lysate/alcohol mixture to a solid support; e) eluting the miRNA molecules from the solid support with an ionic solution; and, f) capturing the miRNA molecules. Typically the sample is dried down and resuspended in a liquid and volume appropriate for subsequent manipulation.

V. Cancer Treatment

Cancers that may be treated or prevented by methods and compositions of the invention include cancer cells from the ovary, bladder, blood, bone, bone marrow, brain, breast, colon, esophagus, gastrointestine, gum, head, kidney, liver, lung, nasopharynx, neck, prostate, skin, stomach, testis, tongue, or uterus. In addition, the cancer may specifically be of the following histological type, though it is not limited to these: neoplasm, malignant; angiosarcomas; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; Sertoli cell carcinoma; leydig cell tumor, malignant; lipid cell rumor, malignant; paraganglioma, malignant; extra-mammary paraganglioma, malignant; pheochromocytoma; glomangio sarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangio sarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odonto sarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Moreover, miRNA can be utilized in a primary tumor or a metastasized tumor or to target specific subpopulations of cells within a cancer complex that may play a critical role in promoting its resistance to therapy, progression, recurrence and/or metastasis. These compartments or cells potentially include cancer stem cells, cells involved in creating or inducing the creation of blood vessels, malignant epithelial cells, stromal or connective tissue cells important for and/or cells important for creating specific niches that promote cancer growth survival or metastasis.

In order to increase the effectiveness of a cancer treatment, it may be desirable to combine the treatment with one or more miRNAs of the invention effective to enhance the cancer treatment. A cancer treatment is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. In some embodiments, they could inhibit the ability of specific cells to generate progeny capable of re-populating tumor recurrences, as cancer stem cells are now believed to do. Similarly, this may involve the differentiation of specific subpopulations of tumor cells into new types of tissues, such as blood vessels capable of supporting continued tumor growth. These processes may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s). In the context of the present invention, it is contemplated that microRNA therapy could be used similarly in conjunction with chemotherapeutic, immunotherapeutic, and/or hormone therapy intervention. It is expected that the treatment cycles would be repeated as necessary. It also is contemplated that various standard therapies, as well as surgical intervention, may be applied in combination with the described hyperproliferative cell therapy. Exemplary additional therapies include surgery, chemotherapy, radiation, hormone therapy, immunotherapy, and or a combination thereof.

VI. Methods and Materials for Production of miRNA

The microRNAs of the invention can be isolated from cells or tissues, recombinantly produced, or synthesized in vitro by a variety of techniques well known to one of ordinary skill in the art, for example.

In one embodiment, miRNA is isolated from cells or tissues. Techniques for isolating miRNA from cells or tissues are well known to one of ordinary skill in the art. For example, miRNA can be isolated from total RNA using the mirVana miRNA isolation kit from Ambion, Inc. Another technique utilizes the flashPAGE™ Fractionator System (Ambion, Inc.) for PAGE purification of small nucleic acids.

The miRNA can be obtained by preparing a recombinant version thereof (i.e., by using the techniques of genetic engineering to produce a recombinant nucleic acid which can then be isolated or purified by techniques well known to one of ordinary skill in the art). This embodiment involves growing a culture of host cells in a suitable culture medium, and purifying the miRNA from the cells or the culture in which the cells are grown. For example, the methods include a process for producing a miRNA in which a host cell containing a suitable expression vector that includes a nucleic acid encoding a miRNA is cultured under conditions that allow expression of the encoded miRNA. In a preferred embodiment the nucleic acid encodes the microRNA. The miRNA can be recovered from the culture, from the culture medium or from a lysate prepared from the host cells, and further purified. The host cell can be a higher eukaryotic host cell such as a mammalian cell, a lower eukaryotic host cell such as a yeast cell, or the host cell can be a prokaryotic cell such as a bacterial cell. Introduction of a vector containing the nucleic acid encoding the miRNA into the host cell can be effected by calcium phosphate transfection, DEAE, dextran mediated transfection, or electroporation (Davis, L. et al., Basic Methods in Molecular Biology (1986)).

Any host/vector system can be used to express one or more of the miRNAs. These include, but are not limited to, eukaryotic hosts such as HeLa cells and yeast, as well as prokaryotic host such as *E. coli* and *B. subtilis*. miRNA can be expressed in mammalian cells, yeast, bacteria, or other cells where the miRNA gene is under the control of an appropriate promoter. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989). In the preferred embodiment, the miRNA is expressed in mammalian cells. Examples of mammalian expression systems include C, 127, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells. Mammalian expression vectors may comprise an origin of replication, a suitable promoter, polyadenylation site, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Potentially suitable yeast strains include *Saccharomyces cerevisiae, Schizosaccharomyces pombe, Kluyveromyces* strains, *Candida*, or any yeast strain capable of expressing miRNA. Potentially suitable bacterial strains include *Escherichia coli, Bacillus subtilis, Salmonella typhimurium,* or any bacterial strain capable of expressing miRNA.

The miRNA may be prepared by culturing transformed host cells under culture conditions suitable to express the miRNA. The resulting expressed miRNA may then be purified from such culture (i.e., from culture medium or cell extracts) using known purification processes, such as gel filtration and ion exchange chromatography. The purification of the miRNA may also include an affinity column containing agents which will bind to the protein; one or more column steps over such affinity resins as concanavalin A-agarose, Heparin-Toyopearl™ or Cibacrom blue 3GA Sepharose™; one or more steps involving hydrophobic interaction chromatography using such resins as phenyl ether, butyl ether, or propyl ether; immunoaffinity chromatography, or complementary cDNA affinity chromatography.

The miRNA may also be expressed as a product of transgenic animals, which are characterized by somatic or germ cells containing a nucleotide sequence encoding the miRNA. A vector containing DNA encoding miRNA and appropriate regulatory elements can be inserted in the germ line of animals using homologous recombination (Capecchi, Science 244:1288-1292 (1989)), such that the express the miRNA. Transgenic animals, preferably non-human mammals, are produced using methods as described in U.S. Pat. No. 5,489,743 to Robinson, et al., and PCT Publication No. WO 94/28122 by Ontario Cancer Institute. miRNA can be isolated from cells or tissue isolated from transgenic animals as discussed above.

In a preferred embodiment, the miRNA can be obtained synthetically, for example, by chemically synthesizing a nucleic acid by any method of synthesis known to the skilled artisan. The synthesized miRNA can then be purified by any method known in the art. Methods for chemical synthesis of nucleic acids include, but are not limited to, in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

In some circumstances, for example, where increased nuclease stability is desired, nucleic acids having nucleic acid analogs and/or modified internucleoside linkages may be preferred. Nucleic acids containing modified internucleoside linkages may also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($-CH_2-S-CH_2$), dimethylene-sulfoxide ($-CH_2-SO-CH_2$), dimethylene-sulfone ($-CH_2-SO_2-CH_2$), 2'-O-alkyl, and 2'-deoxy-2'-fluoro phosphorothioate internucleoside linkages are well known in the art (see Uhlmann et al., 1990, Chem. Rev. 90:543-584; Schneider et al., 1990, Tetrahedron Lett. 31:335 and references cited therein). U.S. Pat. Nos. 5,614,617 and 5,223,618 to Cook, et al., U.S. Pat. No. 5,714,606 to Acevedo, et al., U.S. Pat. No. 5,378,825 to Cook, et al., U.S. Pat. Nos. 5,672,697 and 5,466,786 to Buhr, et al., U.S. Pat. No. 5,777,092 to Cook, et al., U.S. Pat. No. 5,602,240 to De Mesmaeker, et al., U.S. Pat. No. 5,610,289 to Cook, et al. and U.S. Pat. No. 5,858,988 to Wang, also describe nucleic acid analogs for enhanced nuclease stability and cellular uptake.

VII. Methods of Treatment

Methods for enhancement of treatment or prevention of at least one symptom or manifestation of cancer are provided including administration of an effective amount of a composition containing a microRNA miRNA 520-a, g, and/or h nucleic acid molecule to alleviate at least one symptom or decrease at least one manifestation. In an embodiment, the cancer is ovarian. The compositions described herein can be administered in effective dosages alone or in combination with cancer therapy such as chemotherapy, immunotherapy, radiation therapy, and/or hormonal or other targeted therapy to provide a beneficial effect for treatment, e.g. reduce the dosage of anti-cancer therapy and/or reduce the duration of treatment and/or reduce the number of administrations of treatment; reduce cycle number, tumor size, reduce cell proliferation of the tumor, inhibit angiogenesis, inhibit metastasis, or otherwise improve at least one symptom or manifestation of the disease. These can include combinations of treatments that do not directly target tumor cells, but instead enhance systemic responses designed to target tumor cells or alleviate symptoms, such as immunotherapy. Combinations of miR-520a/g/h treatments could be used to potentiate the response of interventions designed to impact the immune response to a patient's cancer even though the use of miR-520g/h/a treatment may or may not directly alter patterns of gene expression or responses of immune cells themselves. Mir-520g/h/a in combination with radiation therapy is used to enhance response to therapy, in particular aspects.

The compositions are administered to an individual in need of treatment of at least one symptom or manifestation (since disease can occur/progress in the absence of symptoms) of cancer. The individual may be at risk for cancer, such as having personal or family history, be a tobacco user, have genetic marker(s) and so forth. In some cases, the therapy acts as a radiation or chemotherapy sensitizer, for example. The compositions described herein can be administered to a subject prior to administration of a cytotoxic therapy in an amount effective to sensitize cells or tissues to be treated to the effects of the cytotoxic therapy. In one embodiment the cytotoxic therapy is radiotherapy. In another embodiment the cytotoxic therapy is chemotherapy. Sensitization describes a condition of the cells or tissues to be treated in which prior administration of the compositions described herein increases at least one effect of the cytotoxic therapy on the cells or tissues relative to cells or tissues not receiving prior administration of the compositions described herein. The increased effect may be on reduction of tumor size, reduction in cell proliferation of a tumor, inhibition of angiogenesis, inhibition of metastasis, or improvement of at least one symptom or manifestation of the disease.

VIII. Method of Administration

In general, methods of administering nucleic acids are well known in the art. In particular, the routes of administration already in use for nucleic acid therapeutics, along with formulations in current use, provide preferred routes of administration and formulation for the nucleic acids described above.

Nucleic acid compositions can be administered by a number of routes including, but not limited to: oral, intravenous, intraperitoneal, intramuscular, transdermal, subcutaneous, topical, sublingual, direct tumor injection, or rectal means. Nucleic acids can also be administered via liposomes or nanoparticles. Such administration routes and appropriate formulations are generally known to those of skill in the art. In specific embodiments, the compositions of the invention are injected intravenously as end modified miRNA mimics.

Administration of the formulations described herein may be accomplished by any acceptable method that allows the miRNA or nucleic acid encoding the miRNA to reach its target. The particular mode selected will depend of course, upon exemplary factors such as the particular formulation, the severity of the state of the subject being treated, and the dosage required for therapeutic efficacy. As generally used herein, an "effective amount" of a nucleic acid is the amount that is able to treat one or more symptoms of cancer or related disease, reverse the progression of one or more symptoms of cancer or related disease, halt the progression of one or more symptoms of cancer or related disease, or prevent the occurrence of one or more symptoms of cancer or related disease in a subject to whom the formulation is administered, as compared to a matched subject not receiving the compound or therapeutic agent. The actual effective amounts of drug can vary according to the specific drug or combination thereof being utilized, the particular composition formulated, the mode of administration, and the age, weight, condition of the patient, and severity of the symptoms or condition being treated.

Any acceptable method known to one of ordinary skill in the art may be used to administer a formulation to the subject. The administration may be localized (i.e., to a particular region, physiological system, tissue, organ, or cell type) or systemic, depending on the condition being treated.

Injections can be e.g., intravenous, intradermal, subcutaneous, intramuscular, intratumoral, or intraperitoneal. The composition can be injected intradermally for treatment or prevention of cancer, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

Preferably, the agent and/or nucleic acid delivery system are provided in a manner which enables tissue-specific uptake of the agent and/or nucleic acid delivery system. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

The formulations may be delivered using a bioerodible implant by way of diffusion or by degradation of the polymeric matrix. In certain embodiments, the administration of the formulation may be designed so as to result in sequential exposures to the miRNA over a certain time period, for example, hours, days, weeks, months or years. This may be accomplished, for example, by repeated administrations of a formulation or by a sustained or controlled release delivery system in which the miRNA is delivered over a prolonged period without repeated administrations. Administration of the formulations using such a delivery system may be, for example, by oral dosage forms, bolus injections, transdermal patches or subcutaneous implants. Maintaining a substantially constant concentration of the composition may be preferred in some cases.

Other delivery systems suitable include, but are not limited to, time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants, or polymer-based compositions. Specific examples include, but are not limited to, erosional systems in which the miRNA is contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the miRNA. In addition, a pump-based hardware delivery system may be used to deliver one or more embodiments.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose-administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the miRNA employed and the condition of the patient, as well as the body weight or surface area of the patient to be treated. The size of the dose is also determined by the existence, nature, and extent of any adverse side-effects that accompany the administration of a particular vector, and formulation, in a particular patient.

Therapeutic compositions comprising one or more nucleic acids are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of treatment versus non-treatment (e.g., comparison of treated vs. untreated cells or animal models), in a relevant assay. Formulations are administered at a rate determined by the LD50 of the relevant formulation, and/or observation of any side-effects of the nucleic acids at various concentrations, e.g., as applied to the mass and overall health of the patient. Administration can be accomplished via single or divided doses.

In vitro models can be used to determine the effective doses of the nucleic acids as a potential cancer treatment. Suitable in vitro models include, but are not limited to, proliferation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., J. Natl. Can. Inst., 52: 921-30 (1974), mobility and invasive potential of tumor cells in Boyden Chamber assays as described in Pilkington et al., Anticancer Res., 17: 4107-9 (1997), and angiogenesis assays such as induction of vascularization of the chick chorioallantoic membrane or induction of vascular endothelial cell migration as described in Ribatta et al., Intl. JS. Dev. Biol., 40: 1189-97 (1999) and Li et al., Clin. Exp. Metastasis, 17:423-9 (1999), respectively. Suitable tumor cells lines are available, e.g. from American Type Tissue Culture Collection catalogs.

In vivo models are the preferred models to determine the effective doses of nucleic acids described above as potential cancer treatments. Suitable in vivo models include, but are not limited to, mice that carry a mutation in the KRAS oncogene (Lox-Stop-Lox K-Ras$^{G12D}$ mutants, Kras2$^{tm4Tyj}$) available from the National Cancer Institute (NCI) Frederick Mouse Repository. Other mouse models known in the art and that are available include but are not limited to models for gastrointestinal cancer, hematopoietic cancer, lung cancer, mammary gland cancer, nervous system cancer, ovarian cancer, prostate cancer, skin cancer, cervical cancer, oral cancer, and sarcoma cancer.

In determining the effective amount of the miRNA to be administered in the treatment or prophylaxis of disease the physician evaluates circulating plasma levels, formulation toxicities, and progression of the disease.

The dose administered to a 70 kilogram patient is typically in the range equivalent to dosages of currently-used therapeutic antisense oligonucleotides such as Vitravene® (fomivirsen sodium injection) which is approved by the FDA for treatment of cytomegaloviral RNA, adjusted for the altered activity or serum half-life of the relevant composition.

The formulations described herein can supplement treatment conditions by any known conventional therapy, including, but not limited to, antibody administration, vaccine administration, administration of cytotoxic agents, natural amino acid polypeptides, nucleic acids, nucleotide analogues, and biologic response modifiers. Two or more combined compounds may be used together or sequentially. For example, the nucleic acids can also be administered in therapeutically effective amounts as a portion of an anti-cancer cocktail. An anti-cancer cocktail is a mixture of the oligonucleotide or modulator with one or more anti-cancer drugs in addition to a pharmaceutically acceptable carrier for delivery. The use of anti-cancer cocktails as a cancer treatment is routine. Anti-cancer drugs that are well known in the art and can be used as a treatment in combination with the nucleic acids described herein include, but are not limited to: Actinomycin D, Aminoglutethimide, Asparaginase, Bleomycin, Busulfan, Carboplatin, Carmustine, Chlorambucil, Cisplatin (cis-DDP), Cyclophosphamide, Cytarabine HCl (Cytosine arabinoside), Dacarbazine, Dactinomycin, Daunorubicin HCl, Doxorubicin HCl, Estramustine phosphate sodium, Etoposide (V16-213), Floxuridine, 5-Fluorouracil (5-Fu), Flutamide, Hydroxyurea (hydroxycarbamide), Ifosfamide, Interferon Alpha-2a, Interferon Alpha-2b, Leuprolide acetate (LHRH-releasing factor analog), Lomustine, Mechlorethamine HCl (nitrogen mustard), Melphalan, Mercaptopurine, Mesna, Methotrexate (MTX), Mitomycin, Mitoxantrone HCl, Octreotide, Plicamycin, Procarbazine HCl, Streptozocin, Tamoxifen citrate, Thioguanine, Thiotepa, Vinblastine sulfate, Vincristine sulfate, Amsacrine, Azacitidine, Hexamethylmelamine, Interleukin-2, Mitoguazone, Pentostatin, Semustine, Teniposide, and Vindesine sulfate.

IX. Chemotherapeutic Agents

These can be, for example, agents that directly cross-link DNA, agents that intercalate into DNA, and agents that lead to chromosomal and mitotic aberrations by affecting nucleic acid synthesis. Agents that directly cross-link nucleic acids, specifically DNA, are envisaged and are shown herein, to eventuate DNA damage leading to a synergistic antineoplastic combination. Agents such as cisplatin, and other DNA alkylating agents may be used. Agents that damage DNA also include compounds that interfere with DNA replication, mitosis, and chromosomal segregation. Examples of these compounds include adriamycin (also known as doxorubicin), VP-16 (also known as etoposide), podophyllotoxin, and the like. Widely used in clinical setting for the treatment of neoplasms, these compounds are administered, for example, through bolus injections intravenously at doses ranging from 25-100 mg/m$^2$ at 21 day intervals for adriamycin, to 35-100 mg/m$^2$ for etoposide intravenously or orally.

Examples of alternate strategies for targeting ovarian cancer include agents that inhibit the activity of poly ADP ribose polymerase (PARP), such as Iniparib (BSI 201), Olaparib (AZD-2281) Rucaparib (AG014699, PF-01367338), Veliparib, MK4827 or BMN673. These agents inhibit the activity of the gene product PARP1 that is involved in the repair of single-strand DNA breaks. If single stranded DNA nicks persist unrepaired, events involved in DNA replication will cause double strand breaks to form and ultimately result in cell death as injured cells attempt to proceed through mitosis. In particular, cells with defects in homologous recombination, including cells defective in BRCA1/2, Rad51 and others are particularly sensitive to the biologic effects of PARP inhibitors, as cells with these defects are unable repair the double stranded DNA breaks that ultimately result from inhibition of PARP1 activity. In contrast, healthy cells able to repair double stranded DNA nicks are relatively insensitive to these agents, hence the description of this strategy in the art as "synthetic lethal". In certain embodiments of the invention, one or more synthetic lethal compositions are employed in conjunction with the miRNAs of the invention, either in succession or at the same time.

Exemplary chemotherapeutics include at least 1) antibiotics, such as doxorubicin, daunorubicin, mitomycin, Actinomycin D; 2) platinum-based agents, such as cisplatin; 3) plant alkaloids, such as taxol and vincristine, vinblastine; 4) alkylating agents, such as carmustine, melphalin, cyclophosphamide, chlorambucil, bisufan, an dlomustine.

X. Immunotherapy

In some embodiments of the invention, one or more microRNAs are employed to enhance immunotherapy cancer treatment in an individual. In specific aspects, the immunotherapy comprises monoclonal antibodies, immune modulating agents known to modify sensitivity or function of the immune response, administration of cytokines or cytokine derivatives known to other agents or mileus in which immune responses to cancers and other diseases are generated, administration of adjuvants designed to enhance the immunogenticity of specific antigens to challenge or modify immune responses.

Several of the newer chemotherapy agents are monoclonal antibodies. Monoclonal antibodies work by attaching to certain parts of the tumor-specific antigens and make them easily recognizable to the body's immune system. Some prevent growth of cancer tumors by blocking the cell receptors to the body's "growth factors".

The first one was approved for cancer treatment by the Food and Drug Administration (FDA) in 1997. Alemtuzumab (Campath®), Bevacizumab (Avastin®), Cetuximab (Erbitux®), Gemtuzumab (Mylotarg®), Ibritumomab (Zevalin®), Panitumumab (Vectibix®), Rituximab (Rituxan®), Tositumomab (Bexxar®), and Trastuzumab (Herceptin®) are some of the FDA-approved monoclonal drugs used in cancer treatments.

Monoclonal antibodies (abbreviated MAbs) are useful in treating at least colon, lung, head, neck, and breast cancers. Monoclonal drugs are also used to treat chronic lymphocytic leukemia, acute myelogenous leukemia, and non-Hodgkin's lymphoma.

XI. Hormone Therapy

In some embodiments of the invention, one or more microRNAs are employed to enhance hormone therapy cancer treatment in an individual. Hormone therapy is a form of systemic therapy that is most often used to help reduce the risk of the cancer coming back after surgery, but it may also be used for cancer that has spread or come back after treatment, for example. The therapy may include drugs to block hormones or drugs that change hormone levels.

The female hormone estrogen, for example promotes the growth of breast cancer cells in some women (those who have hormone receptor-positive cancers). For these women, actions are taken to block the effect of estrogen or lower its levels in order to treat breast cancer. Drugs used to block estrogen Tamoxifen and toremifene (Fareston®): Drugs like tamoxifen can be given to block estrogen. Tamoxifen is taken in pill or liquid form, usually every day for up to 5 years after surgery, to reduce the risk the cancer will come back. This drug helps women with early breast cancer if their cancer has hormone receptors (is ER-positive or PR-positive). It is also used to treat hormone receptor-positive breast cancer that has spread and to reduce the risk of breast cancer in women who are at high risk.

Toremifene works like tamoxifen, but is not used as often and is only approved for patients with metastatic breast cancer. The side effects of these drugs are similar.

Fulvestrant: Fulvestrant (Faslodex®) is a drug that blocks the estrogen receptor and then damages it. It often works even if the breast cancer is no longer responding to tamoxifen. It is given as a shot once a month. Hot flashes, mild nausea, and tiredness are the major side effects. Right now it is only used in postmenopausal women with advanced breast cancer that no longer responds to tamoxifen or toremifene.

Drugs used to change hormone that include both direct receptor antagonists (tamoxifen, flutamide), selective receptor agonists/antagonists, agents that target steroid receptor co-activators or co-repressors as well as other agents designed to impact or alter circulating levels of hormones including levels include aromatase inhibitors (AIs), such as: anastrazole (Arimidex®), exemestane (Aromasin®), and letrozole (Femara®), for example. Androgens and androgen antagonists may be employed.

XII. Pharmaceutical Preparations

Pharmaceutical compositions of the present invention comprise an effective amount of one or more microRNAs dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one microRNA or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The microRNA may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The microRNA may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include microRNA, one or more lipids, and an aqueous solvent. These can also be combined into multi-stage vectors that have both liposomes as well as carriers for those liposomes that may be of any range of a material including silicon and others. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the microRNA may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the microRNA are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, microRNA may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound microRNA may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

XIII. Kits of the Invention

Kits are also included as part of the invention. Kits for implementing methods of the invention described herein are specifically contemplated. In some embodiments, there are kits for treating and/or preventing cancer. In some embodiments, the kit comprises one or more 19q13.41 microRNAs and optionally a cancer treatment.

In some embodiments, kit comprises in suitable container means, one or more of the following: 1) poly(A) polymerase; 2) nucleotides (G, A, T, C, and/or U); 3) poly(A) polymerase buffer; reaction buffer; 4) solutions for preparing, isolating, enriching, and/or purifying miRNAs. Other reagents include those generally used for manipulating RNA, such as formamide, loading dye, ribonuclease inhibitors, and DNase. Buffers, as well as other solutions, are contemplated to have a pH of about, at least about, or at most about 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0 or more (or any range derivable therein) in certain embodiments of the invention. Pharmaceutical carriers for the microRNA composition may or may not be included in the kit.

Although in some embodiments the kit comprises the microRNA composition, in other embodiments the microRNA composition is synthesized. Poly(A) polymerase may be from any source, but specifically contemplated is a poly(A) polymerase from yeast or *E. coli*, which may be recombinant or purified from the organism. A reaction buffer for poly(A) polymerase may be included in any kit of the invention. Typically, such a poly(A) polymerase reaction buffer includes a volume exclusion reagent, such as PEG, magnesium, and sodium. In certain embodiments, the poly(A) polymerase reaction buffer in the kit contains at least: about 5, 6, 7, 8, 9, 10, 11, 12, 13, 14, 15% or more (or any range derivable therein) PEG; about 5, 10, 15, 20, 25, 30, 35, 40, 45, 50 mM or more $MgCl_2$ (or any range derivable therein); about 100, 200, 300, 400, 500, 600, 700, 800, 900 mM NaCl (or any range derivable therein); about 50, 60, 70, 80, 90, 100, 110, 120, 130, 140, 150 mM or more MES (or any range derivable therein); and about 0.5, 1, 1.5, 2, 2.5, 3, 3.5, 4 mM or more DTT (or any range derivable therein) The kits may also include a manganese source, which may be included as a separate component of a kit or in a solution or buffer with other components, such as in the reaction buffer It is contemplated that about 5, 10, 15, 20, 25, 30, 35, 40, 45, 50 mM or more of $MnCl_2$ is included m the kit Nucleotides may also be included in kits of the invention. Nucleotides may be for DNA or RNA. Concentrations of a nucleotide or of a nucleotide mix (total concentration of all nucleotides) include, but are not limited to, about, at least about, or at most about 0.5, 1.0, 1 5, 2 0, 2.5, 3.0, 3.5, 4.0, 4.5, 5.0, 5 5, 6.0, 6.5, 7 0, 7.5, 8 0, 8 5, 90, 9 5, 10 0 mM or more (or any range derivable therein) Moreover, they may be modified or not modified. If they are modified, they may have a reactive group or they may have a label attached to it In certain embodiments, one or more nucleotides in a kit has a reactive group, such as an amine-reactive group In other embodiments, a nucleotide is already labeled. It may be labeled with a chemiluminescent or fluorescent label, such as a dye. Specifically contemplated are amine-reactive dyes. Moreover, it is specifically contemplated that kits may or may not contain both modified and unmodified nucleotides. Also, kits may contain the label that will be attached to the nucleotide. Any label that can be attached to a nucleotide, as well as any specifically identified herein, can be included in kits of the invention.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

For any kit embodiment, there can be nucleic acid molecules that comprise a sequence that is identical to all or part of SEQ ID NO:1, SEQ ID NO:2, or SEQ ID NO:3, or variants thereof. Any nucleic acid described herein may be implemented as part of a kit.

The components of the kits may be packaged either in aqueous media or in lyophilized form.

The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

Such kits may also include components that facilitate isolation of the labeled miRNA It may also include components that preserve or maintain the miRNA or that protect against its degradation Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented Kits of the invention may also include one or more of the following: Control RNA; nuclease-free water, RNase-free containers, such as 1.5 ml tubes; RNase-free elution tubes, PEG or dextran, ethanol; acetic acid, sodium acetate; ammonium acetate; guanidinium, detergent; nucleic acid size marker, RNase-free tube tips; and RNase or DNase inhibitors.

It is contemplated that such reagents are embodiments of kits of the invention. Such kits, however, are not limited to the particular items identified above and may include any reagent used for the manipulation or characterization of miRNA.

In some embodiments of the invention, additional anti-cancer agents are included in the kit. Examples include chemotherapeutics, hormone therapy agents, and immunotherapy agents.

EXAMPLES

The following examples are included to demonstrate some embodiments of the invention. It should be appreciated by those of skill in the art that the techniques disclosed in the examples which follow represent techniques discovered by the inventor to function well in the practice of the invention, and thus can be considered to constitute some modes for its practice. However, those of skill in the art should, in light of the present disclosure, appreciate that many changes can be made in the specific embodiments which are disclosed and still obtain a like or similar result without departing from the spirit and scope of the invention.

Example 1

Use of miR-520G/H to Sensitize Epithelial Ovarian Cancers to Chemotherapy

MicroRNAs (miRNAs) are small, non-coding RNA transcripts that play a critical role in silencing patterns of gene expression. To identify microRNAs useful as therapeutic targets for epithelial ovarian cancer, the genomic location of known human microRNAs was determined using MirBase and correlated with genomic copy number variation identified in a dataset of >400 ovarian cancer specimens. In aspects of the invention, microRNAs whose patterns of gene expression are either tightly repressed or lost during the course of treatment for ovarian cancer are useful for therapeutically targeting cancers, including ovarian cancers, for example. The inventors identified a unique genomic locus at 19q13.41 that encodes more than 48 individual microRNAs. Copy number losses at this locus could be identified in ~37% of high grade papillary serous cancers. Expression of individual 19q locus microRNAs did not appear to be a prominent feature of reproductive tract tissues or cancers. Mimics for at least 3 of the microRNAs encoded by the 19q13.41 locus (mir-520a-3p, miR-520-5p, miR-520h) significantly impacted either proliferation or apoptosis in established ovarian cancer cell lines (SKOV4, HEY, OVCAR8, OVCAR5) when compared to control cultures. Of these, miR-520a and miR-520h decreased the $IC_{50}$ of multiple ovarian cancer cell lines for cisplatin as much as 3-fold ($p<0.01$), regardless of their impact on caspase activity. In examples of the invention, targets for miR-520a and miR-520h include >150 gene products previously implicated, for example, in DNA damage pathways and ovarian cancer, including ATM, BRCA1, FANCD2, Bcl-2, AKT and E2F, for example. In exemplary OVCAR8 cells, ectopic expression of miR-520h induced both the phosphorylation and degradation of ATM, targeted Caspase 7 and blunted the response of BRCA1 and other members of DNA damage repair pathways to increasing concentrations of cisplatin.

Altered genomic copy number variation at the 19q13.41 microRNA locus occurs frequently in cancers including epithelial ovarian cancers, and individual microRNAs encoded by this locus are useful to sensitize ovarian cancers to platinum-based chemotherapy, for example. By routine methods in the art, one can determine how these microRNAs exert their biologic effects, identify genetic signatures predictive of their ability to sensitize primary ovarian cancers to chemotherapy and determine how best and when to deliver specific miR520-a, g, and/or h microRNAs for optimal therapeutic impact.

Example 2

Exemplary Materials and Methods

Cell Culture and In Vitro Assays

Established ovarian cancer cell lines were obtained from the ATCC (OVCAR8, OVCAR5) and the University of Texas M.D. Anderson Cancer Center (HEYA8, SKOV3ip1). All cell lines were maintained at 37° C. in RPMI 1640 media (Invitrogen, Carlsbad, Calif.) supplemented with 10% fetal bovine serums (Hyclone, Logan, Utah) and 1% penicillin/streptomycin (Gibco, Carlsbad, Calif.). MicroRNA mimics and mimic controls (Dharmacon, Lafayette, Colo.) were transiently transfected into actively growing cultures using Lipofectamine 2000 (Invitrogen, Carlsbad, Calif.). After a 24-hour incubation, transfected cultures were washed, passaged and seeded into 96 well plates. Proliferation and apoptosis were measured at 72, 96 and 120 hours after transfection using standard assays (Cell Titer 96 Aqueous One; Caspase Glo 3/7; Promega, Madison, Wis.). pLemiR expression vectors (Open Biosystems/Thermo, Huntsville, Ala.) were prepared according to manufacturer's instructions and transfected into cells using Fugene 6 (Roche, Indianapolis, Ind.). Following transfection, stable clones were selected using puromycin (Invitrogen) at doses optimized for each line. Rates of proliferation and apoptosis were examined in stable transfectants 24, 48, 72 and 96 hours after selected cells had been passaged and dispensed into 96 well plates. Viability was assessed across a clinically relevant range of cisplatin concentrations using an MTS assay (Promega). Cisplatin was obtained from Teva Pharmaceuticals (Irvine, Calif.).

RNA Extraction and Quantitative RT-PCR

Total RNA was extracted from cell pellets using the mirVana miRNA extraction kit (Ambion, Austin, Tex.) according to the manufacturer's instructions. Levels of microRNA expression were examined using Mature MicroRNA Taqman assays (Applied Biosystems, Foster City, Calif.) using U6 as a control. For all gene expression assays, cDNA was prepared using qScript cDNA supermix (Quanta Biosciences, Gaithersburg, Md.). TaqMan gene expression assays (Applied Biosystems) were used to measure expression of specific target genes according to the manufacturer's instructions. All reactions were performed in triplicate using OneStepPlus real time PCR system (Applied Biosystems). All qPCR results are reported using the $\Delta\Delta C_T$ method (17).

Western Blot Analysis

Whole cell lysates equivalent to 30 μg of protein were resolved on 4-12% gradient SDS-PAGE. Resolved proteins were transferred onto PVDF membranes using the iBlot system (Invitrogen). Rabbit polyclonal and/or mouse monoclonal antibodies specifically recognizing ATM, phospo-ATM (Ser1981) CHK1 phospho-CHK1 (Ser216), p21, phospo-CHK2 (Tyr68), BCL2, XIAP, CDC25A were obtained from Cell Signaling Technologies (Danvers, Mass.). A rabbit polyclonal antibody recognizing FANCD2 was also purchased from Abcam (Cambridge, Mass.). Protein expression was visualized using species-specific, horseradish peroxidase-conjugated secondary antibody (Cell Signaling) and ECL Plus chemiluminescent substrate (Amersham, Buckinghamshire, UK).

In Vivo Experiments

Permission to perform animal experiments was obtained from the Institutional Animal Care and Use Committee (IACUC) for Baylor College of Medicine. Eight-week female athymic (Foxn1$^{nu/nu}$) mice were purchased from the National Cancer Institute-Charles River and maintained on a standard diet ad lib. Each animal was inoculated intraperitoneally with $2.5 \times 10^6$ cells stably transfected with vector driving miR-520h, a non-targeting miRNA control or empty vector. Expression of miR-520h was measured in cell lines using Taqman assays immediately prior to inoculation. Tumor xenografts were followed weekly for tumor progression or regression using the Image Station In-Vivo FX system (Kodak Molecular Imaging Systems, New Haven, Conn.) using endogenous RFP encoded by the pLemiR vector as a tag. At each time point, mice were anesthetized with isoflurane and placed in an imaging chamber, after which, fluorescent intensity images with x-ray overlay were obtained and analyzed. At the completion of the study, mice were euthanized after sedation under isoflurane (Abbott Laboratories, North Chicago, Ill.). For experiments involving treatment, cisplatin was administered at 5 mg/kg to mice by tail vein injection weekly for 4 weeks, after which, 1.5 mg/kg was administered biweekly. Tumor volume and distribution for all animals in each experiment were documented and correlated with imaging results.

Example 3

Exemplary Results

To identify microRNAs potentially useful as therapeutic targets in ovarian cancer, the inventors screened known human microRNAs (v15.0) as a function of the copy number variation observed at their genomic loci in a dataset of 500 epithelial ovarian cancers (EOC). Using this data, the inventors identified specific microRNAs that sensitize human cancers to cytotoxic chemotherapy, including miR-520a/g/h. Copy number losses at the genomic locus encoding these miRNAs could be detected in ~37% of ovarian cancer specimens, whereas copy number gains were observed in ~35%. In general, low levels of expression for the individual microRNAs encoded by this locus were observed when the same set of ovarian cancer specimens were screened using a custom miRNA expression array, indicating that levels of the microRNAs encoded by this locus are typically repressed. To more closely examine this question, the inventors interrogated a comprehensive database of microRNA transcripts previously compiled from reproductive tract tissues and ovarian cancers studied using Next Generation Sequencing (NGS). Using this dataset, there was only rare evidence for expression of miR-520a/g/h microRNAs in either distal fallopian tube (n=14) or primary cultures of normal ovarian surface epithelia (n=7). In addition, very few transcripts corresponding to mature miR-520a/g/h microRNAs were identified in epithelial ovarian cancers, regardless of whether papillary serous (n=12), endometrioid (n=6) or clear cell cancers (n=5) were examined. Collectively, these observations indicate that expression of miR-520a/g/h microRNAs are tightly repressed in normal female reproductive tract tissues and that dysregulated expression of 19q13.41 microRNAs occurs, but is not a predominant feature of epithelial ovarian cancers.

To assess the biologic impact of dysregulated 19q locus microRNA expression in those ovarian cancers where they are expressed, the inventors parsed groups of ovarian cancer patients according to levels of 19q cluster microRNAs in a stepwise fashion using data recently generated by the TCGA. Kaplan-Meier analysis was used to compare survival for each group determined in this fashion and define groups of ovarian cancer patients where differences in microRNA expression had their most robust association with outcome demographics. Using this approach, there was a strong correlation between levels of miR-520g/h expression and improved survival when the group of 240 patients with lowest miR-520g/h expression were compared to outcomes for the 120 patients with highest levels of miR-520g/h expression (Z-score of 2.7, p<0.001). These observations indicate that dysregulated expression of miR-520h favorably impacts ovarian cancer outcomes in a specific subset of patients in which levels are expressed beyond an arbitrarily defined threshold.

Expression of Individual 19q13.41 Locus MicroRNAs Acutely Impact Ovarian Cancer Growth and Apoptosis.

Figure 2:
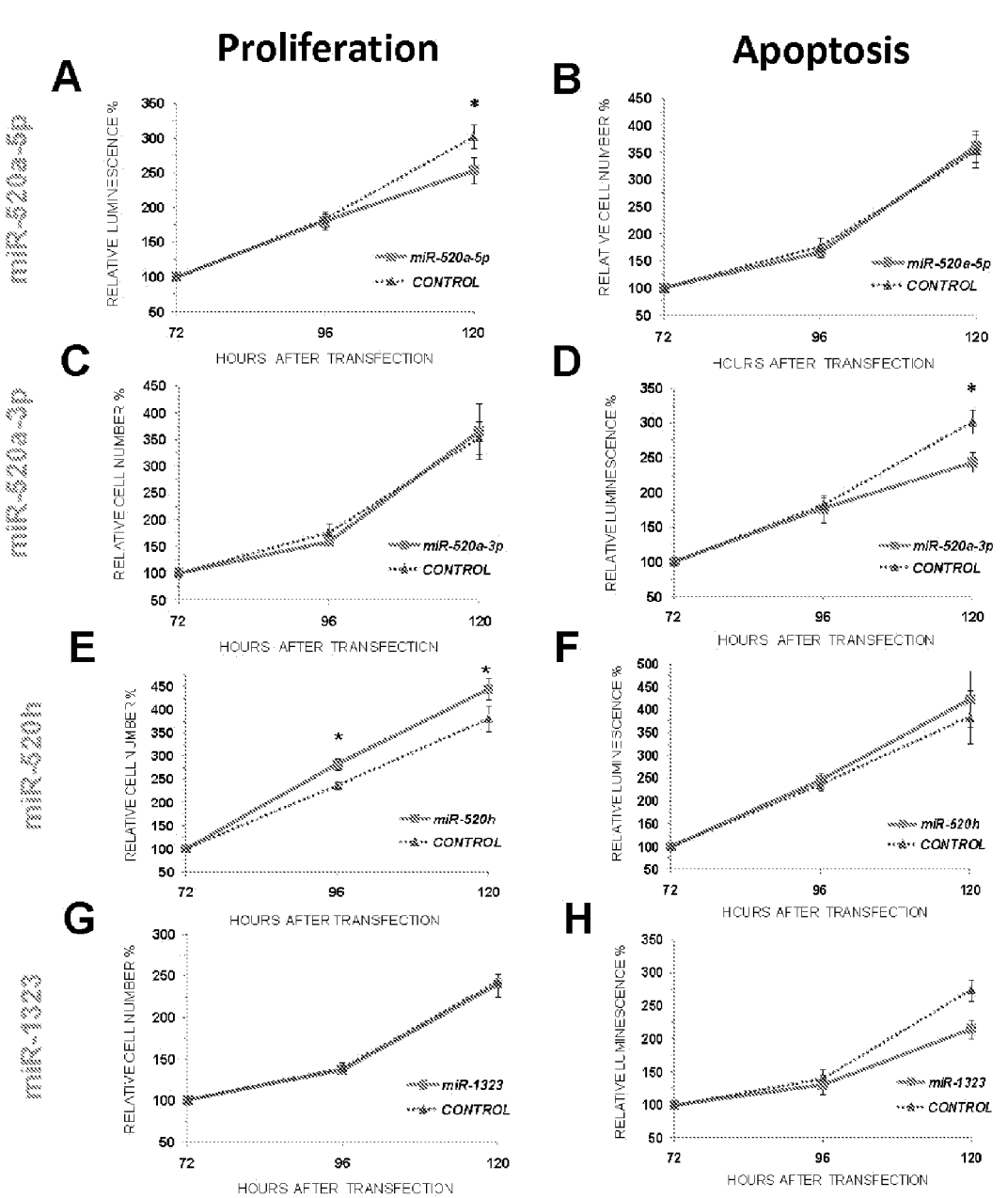
FIG. 2. Impact of Specific microRNAs on Ovarian Cancer Proliferation and Apoptosis. MTS and Caspase Glo 3/7 assays were used to compare rates of proliferation (A,C,E,G) and apoptosis (B,D,F,H) in OVCAR8 cells transiently transfected mimics for miR-520a-3p (A,B), miR-520a-5p (C,D), miR-520h (E,F) and miR-1323 (G,H) or non-silencing controls. Mir-520g/h significantly increased the proliferation (n=12, p<0.001), whereas miR-520a-3p (See 2B, n=12; p=0.008), miR520a-5p (See 2D; n=12; p=0.00 and miR-1323 (see 2H; n=12, p=0.0) decreased apoptosis when compared to OVCAR8 cells transfected with non-silencing microRNA mimic controls transfected under identical conditions. Hairpin microRNA inhibitors were not studied as levels of endogenous 19q locus microRNAs were undetectable (data not shown).
Figure 3:
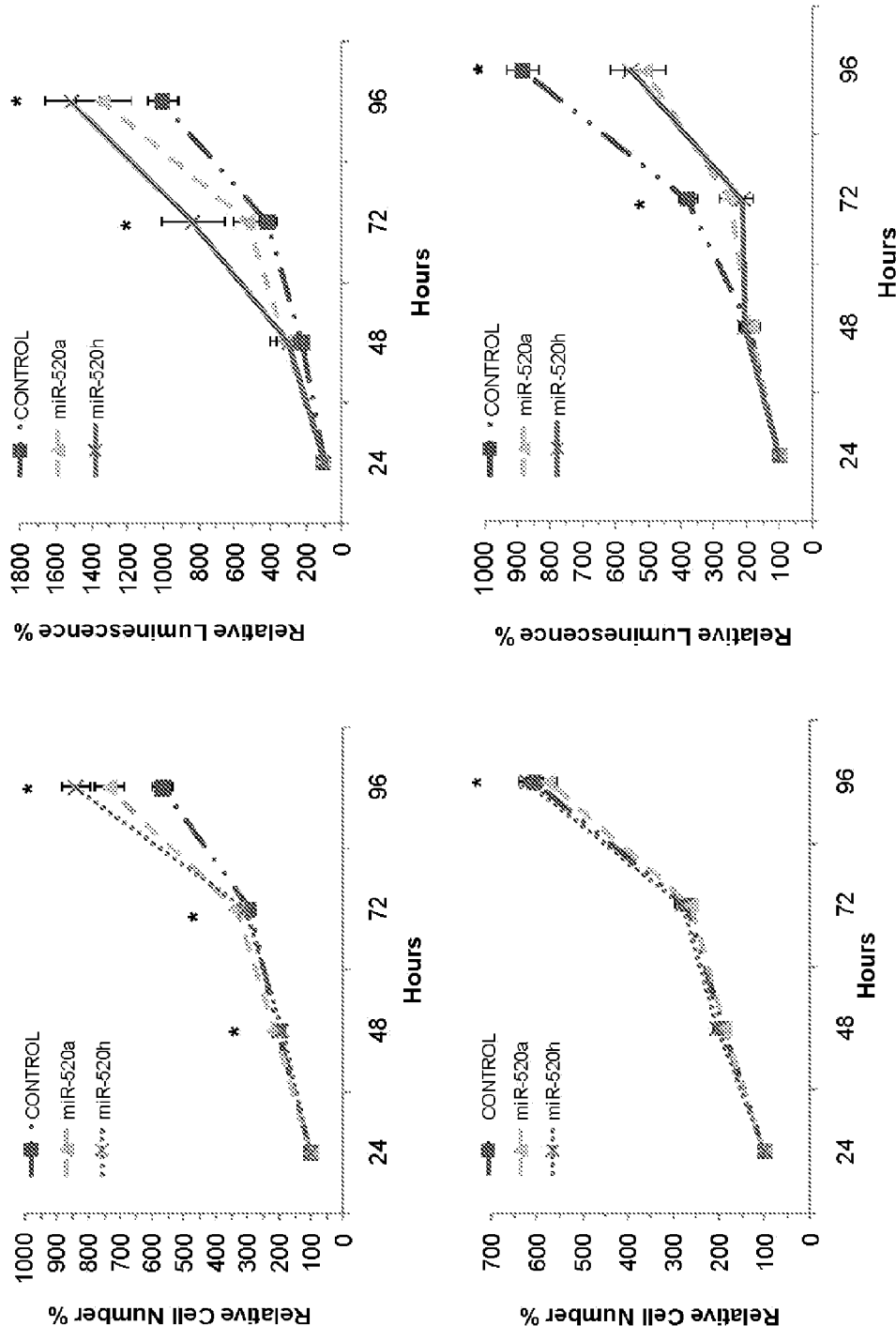
FIG. 3. Ectopic Expression of miR-520h Sensitizes Established Ovarian Cancer Cell Lines to Chemotherapy. Proliferation and Apoptosis assays following acute transfection of both OVCAR8 and SKOV3ip1 cells with miR-520h and miR-520 is shown. miR-520h significantly reduced rates of proliferation while decreasing apoptosis as measured by commercially available Caspase 3/7 assays. Acute transfection of SKOV3ip1 and OVCAR8 cells with synthetic mimic for miR-520a also resulted in decreased rates of apoptosis but only decreased proliferation only in OVCAR8 cells. No cells were exposed to cisplatin or other platinum-based chemotherapy agents in these studies. All differences are significant ($p<0.05$). Error bars reflect standard deviation calculated from biologic replicates.

To explore 19q13.41 locus microRNAs as being useful to therapeutically target ovarian cancer, the inventors transfected mimics for miR-520a/g/h microRNAs into established ovarian cancer cell lines. The expression of different microRNAs encoded by the 19q13.41 genomic locus individually impact the rates of proliferation or apoptosis in these cells. As demonstrated in FIG. 2, mimics for miR-520h increased the proliferation of OVCAR8 cells by an average of 19% (n=6, p<0.001) when compared to non-silencing control 96 hours following transfection (FIG. 2E). However, short-term transfections with mimics for miR-520h had no impact on apoptosis. In contrast, miR-520a-3p and miR-520a-5p decreased apoptosis in OVCAR8 cells by 16%, 20% and 22% respectively, when compared to controls (FIG. 2, n=6 each microRNA, p<0.002). In screening additional cell lines, mimics for miR-520h were found to increase rates of apoptosis by (n=6, p<0.01) when acutely transfected into HEYA8 cells with no significant impact on proliferation. Transfection of miR-520h mimics had no impact on proliferation or apoptosis in either OVCAR5 (n=6) or HEY cells (n=6). Mimics for at least miR-520a and miR-519c impacted proliferation and/or apoptosis in some but not all ovarian cancer cell lines tested.

Figure 4:
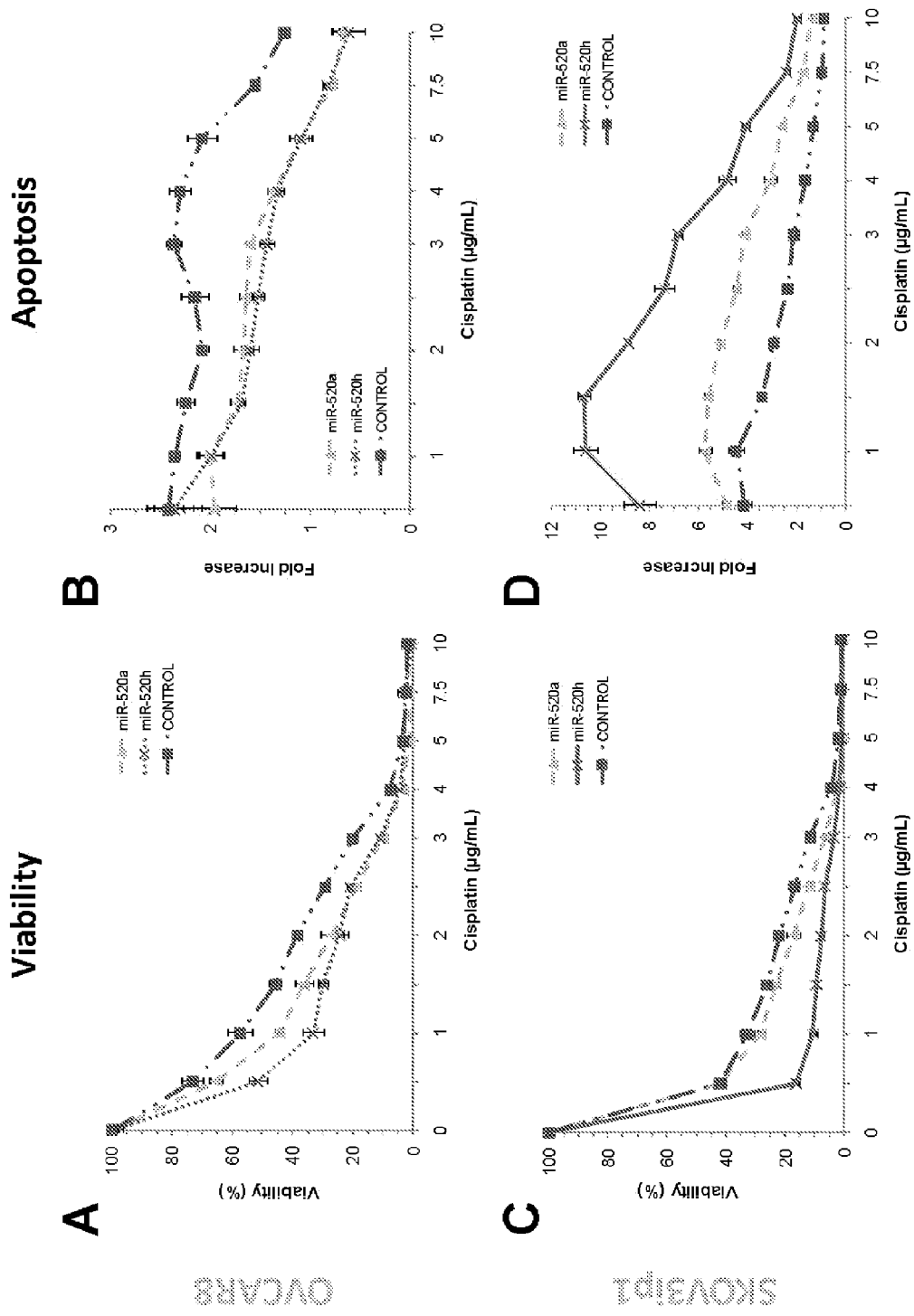
FIGS. 4A-4D. Viability of OVCAR8 and SKOV3ip1 cells stably expressing either microRNA incubated with clinically relevant concentrations of cisplatin. The dose response relationship for cisplatin was established for OVCAR8 and SKOV3ip1 cells stably expressing either miR-520g/h, miR-520a or non-silencing microRNA mimic. The expression of either miR-520g/h or miR-520a sensitized OVCAR8 clones to concentrations of cisplatin <5 μg/mL. This was associated with significantly lower rates of apoptosis at all concentrations of cisplatin tested (up to 10 μg/mL). Both microRNAs also appeared to sensitize SKOV3ip1 cells, although miR-520a appeared to have less impact in SKOV3ip1 than OVCAR8 cells. All differences are significant with $p<0.05$. Error bars reflect standard deviation calculated from 6 biologic replicates.

MiR-520g/h Sensitizes Established Ovarian Cancer Cell Lines to Platinum-Based Chemotherapy Recent evidence suggests that microRNA functions may only become evident under conditions of biologic stress. For this reason, the inventors created clones of OVCAR8 and SKOV3ip1 ovarian cancer cell lines stably expressing either miR-520h (n=3) and miR-520a (n=3). Similar to results with short term transfections, stable expression of miR-520h enhanced the proliferation of both OVCAR8 and SKOV3ip1 cells and inhibited expression caspase 3/7 expression. To assess the impact of these microRNAs on cisplatin-induced cell killing, the inventors examined the viability of OVCAR8 and SKOV3ip1 cells stably expressing either microRNA incubated with clinically relevant concentrations of cisplatin. Stable expression of miR-520h significantly sensitized both OVCAR8 and SKOV3ip1 cells to cisplatinum (FIG. 4C, D). The $IC_{50}$ for cisplatinum in OVCAR8 cells stably expressing miR-520h was 0.54 μg/ml compared to 1.31 μg/ml in OVCAR8 cells expressing a non-targeting mimic control. The $IC_{50}$ for cisplatin in OVCAR8 cells expressing miR-520a was found to be 0.867 μg/ml. For SKOV3ip1 cells, the presence of miR-520h decreased $IC_{50}$ to 0.298 μg/ml as compared to 0.429 μg/ml for cells expressing miR-520a and 0.43 μg/ml for cells expressing the non-silencing control. It should be noted that SKOV3ip1 cells tolerated only very low levels of miR-520a expression. The impact of cisplatin treatment on rates of apoptosis differed dramatically between the two cell lines. In p53 wildtype SKOV3ip1 cells, significantly increased rates of apoptosis were observed in the presence of either miR-520g/h or miR-520a (FIG. 4C,D; n=12, p<0.001 at all time points tested). However, in p53-mutated OVCAR8 cells, significantly decreased levels of apoptosis were observed.

ATM is a Target for miR-520g/h Mediated Gene Silencing in Ovarian Cancers.

Figure 7:
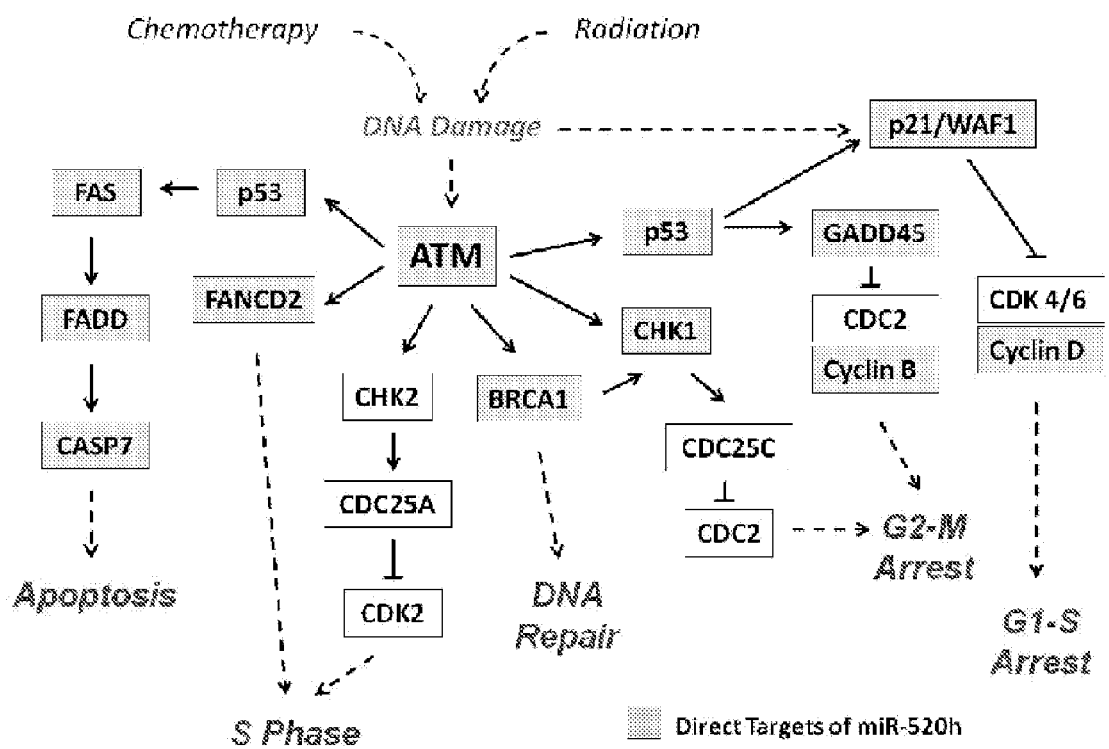
FIG. 7. Model for mir-520h Function in Epithelial Ovarian Cancer. Bioinformatic analysis predict that miR-520h is predicted to directly target multiple gene products involved in critical cell cycle checkpoints (ATM, Cyclin B, Cyclin D, CHK1 and p53), DNA damage repair pathways (FANCD2, BRCA1), and apoptosis (FAS, FADD, Caspase 7).

To better understand the mechanisms by which miR-520g/h impacts ovarian cancer growth, apoptosis and/or metastasis, the inventors used established bioinformatic algorithms (Targetscan, MiRanda) to identify its potential targets in ovarian cancer. They also examined the function of these putative targets using pathway analysis tools including Diana and Ingenuity software. miR-520h was predicted to target more than 3,841 individual genes, including a large number of key oncogenes previously known to be critical for the ongoing progression and/or metastasis of epithelial ovarian cancer. These included FANCD2, ATM, BRCA1, ERα, ERβ, PR, p21/WAF1, FAS, Caspase 7, Cyclin B, Cyclin D, Wee1, XIAP and bcl2. Many of these gene products have been previously implicated in ovarian cancer and are known to play important roles in critical cell functions, including regulation of the G1-S and G2-M cell cycle checkpoints, apoptosis and DNA damage repair pathways. An exemplary model summarizing several findings can be found in FIG. 7.

The bioinformatic analyses indicated that ATM is a critical target mediating the biologic effects of miR-520h in ovarian cancer. To determine whether increased expression of miR-520h targeted ATM for translational silencing, the inventors examined levels of ATM expression in OVCAR8 cells expressing mimics for miR-520g/h. Expression of ATM protein was significantly less in OVCAR8 cells expressing miR-520g/h than control cultures. (FIG. 8A). However, levels of ATM transcript were found to be paradoxically higher in cells expressing miR-520h than non-silencing control when compared by qPCR (FIG. 8C). In addition, the expression of miR-520g/h led to increased levels of an ATM cleavage product (ΔATM) in a dose-dependent fashion when OVCAR8 cells were incubated with increasing concentrations of cisplatin (FIG. 8B; n=3). Generation of this cleavage product has been previously linked to the activation of caspases, including caspase 7, that promote ATM degradation and inactivation. Of note, the relative expression of ATM transcripts in OVCAR8 cells is actually higher in presence of miR-520g/h than non-silencing miRNA control (FIG. 8C). This indicates that the stable expression of miR-520g/h has resulted in increased levels of ATM mRNA in the absence of cisplatin chemotherapy. Presence of mir-520g/h continues to suppress ATM expression at the protein level. In some embodiments this occurs as the direct result of translation inhibition by the miR-520g/h microRNA or in alternative embodiments this is an indirect result of altered caspase expression observed at baseline in these cells (FIG. 8C).

The inventors also examined a number of gene products whose function and/or expression are either predicted by an algorithm to be directly targeted by miR-520h or whose function might be regulated by altered levels of ATM activity. In general, increased expression of miR-520g/h results in decreased levels of the phosphorylated, active form of ATM, consistent with decreased levels of its expression in OVCAR8 cells stably expressing miR-520g/h as well as potentiated degradation of ATM observed when these cells were treated with platinum. However, increased ATM activity does not appear to influence all downstream mediators regulated by this gene product similarly. ATM has been previously shown to regulate CHK1 function by driving its phosphorylation. However, levels of CDC25c expression are much lower in the miR-520g/h expressing cells, particularly when exposed to cisplatin. This finding is explained, in certain embodiments, by the observation that platinum-induced expression of CHK1 is inhibited by miR-520h, likely by direct targeting of the CHK1 transcript for degradation (FIG. 8D). Expression of miR-520g/h blunts the response of additional gene products predicted implicated in DNA damage repair pathways and apoptosis when cells are exposed to cisplatin. As demonstrated in FIG. 8, these gene products include BRCA1 and CASPASE 7. Each of these latter two gene products is predicted to be directly targeted by miR-520g/h. Their responses to cisplatin treatment are significantly less in OVCAR8 clones stably expressing miR-520g/h than clones expressing non-silencing control.

In embodiments of the invention, miR-520g/h works to create a synthetic lethal phenotype in ovarian cancer cells by targeting multiple DNA damage repair pathways. The ability of miR-520g/h to target BRCA1 is an important example of this.

MiR-520g/h Impacts Ovarian Cancer Growth and Metastasis in Vivo

Figure 5:
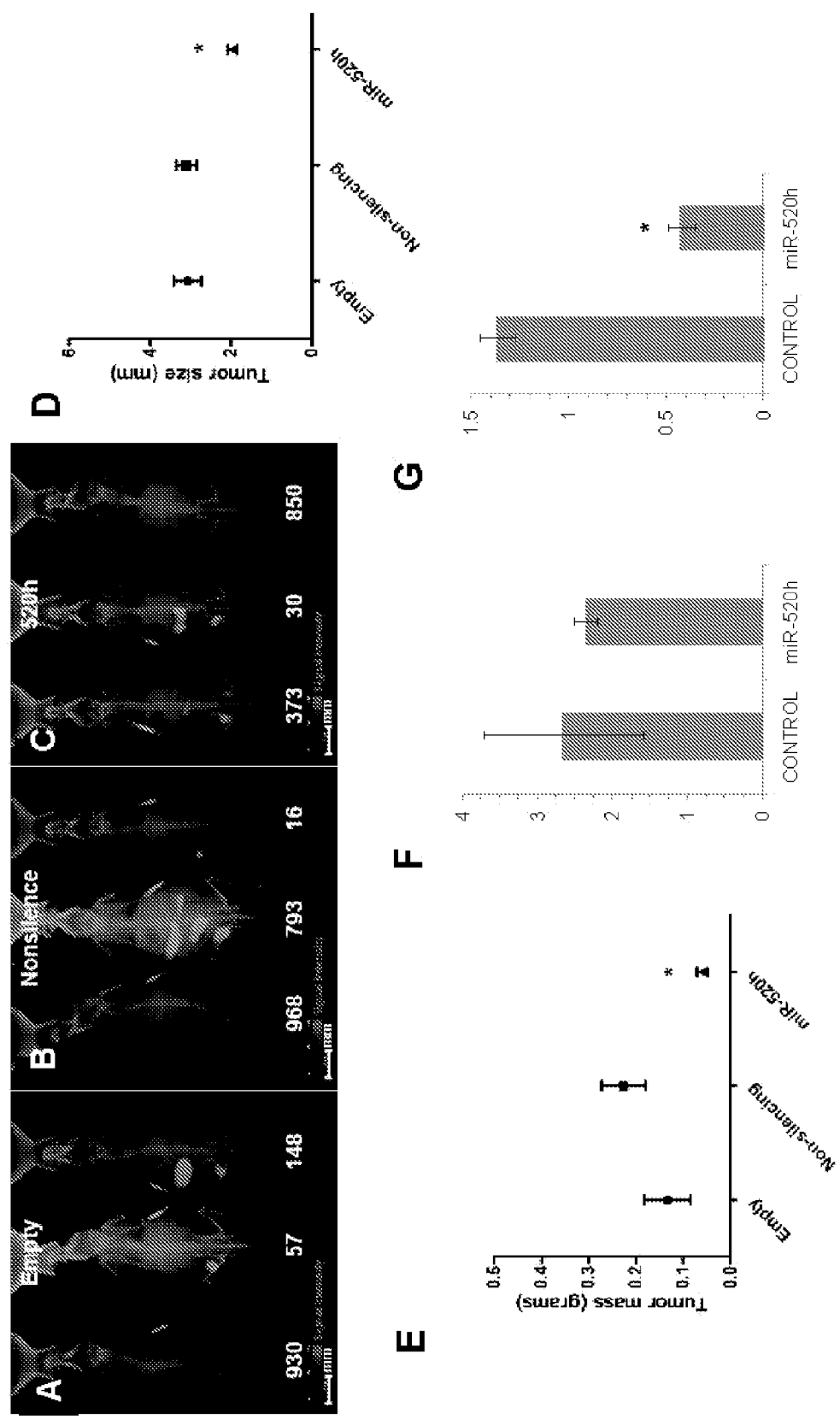
FIG. 5. Overexpression of miR-520g/h alters the growth and metastasis of ovarian cancer xenografts. OVCAR8 cells stably expressing both RFP and either miR-520h (C), non-silencing mimic control (B) or empty vector (A) were injected either intraperitoneally or subcutaneously. All animals were followed for 6 weeks using a whole animal fluorescent imaging system as described to image xenografts in situ. D. Fluorescent imaging demonstrated a large number of smaller implants in animals receiving OVCAR8 cells overexpressing miR-520g/h. (E) These results were confirmed at necropsy when individual implant size was directly measured. (F) Total intraperitoneal tumor burden between the three experiments groups did not differ. (G) Individual implants were also observed when OVCAR8 cells were subcutaneously injected. All differences are significant with $p<0.05$. Error bars reflect standard deviation calculated from 6 biologic replicates.

The in vitro observations indicate that miR520g/h and/or miR-520a alter the proliferations of established ovarian cancer cell lines and in some embodiments are reasonably expected to promote their growth and metastasis in vivo. The inventors utilized xenograft models to characterize this embodiment. Foxn1$^{nu/nu}$ mice were implanted subcutaneously or intraperitoneally with 2.5 million cells stably transfected with miR-520g/h, non-silencing microRNA control or empty vector alone. All animals were then followed, imaging the growth and metastasis of xenografts cells using RFP stably expressed by the ovarian cancer cell line. As demonstrated in FIG. 5A-E, a larger number of smaller xenografts are generated by the intraperitoneal inoculation of OVCAR8 cells stably expressing miR-520g/h than control cells stably transfected with non-coding vector or empty vector alone (n=3, p<0.008). This difference was documented not only when tumor burden was measured according to the number and size of RFP active tumors that met imaging thresholds, but could also directly measured at necropsy (FIG. 5F). Total intraperitoneal tumor burden between the three groups did not differ significantly, indicating that ecptopic expression of miR-520h altered the pattern of cancer metastasis in vivo. Consistent with this consideration, a second experiment was performed where ovarian cancer cells expression miR-520h were compared to cells expressing either a non-targeting miRNA control or empy vector alone. Results of this experiment demonstrate that implant size total tumor burden was significantly smaller in xenografts created by subcutaneous inoculation in a manner that produces a single infiltrative tumor nodule (FIG. 5G).

MiR-520h Improves Survival for Animals Xenografted with Ovarian Cancer Cells

Figure 6:
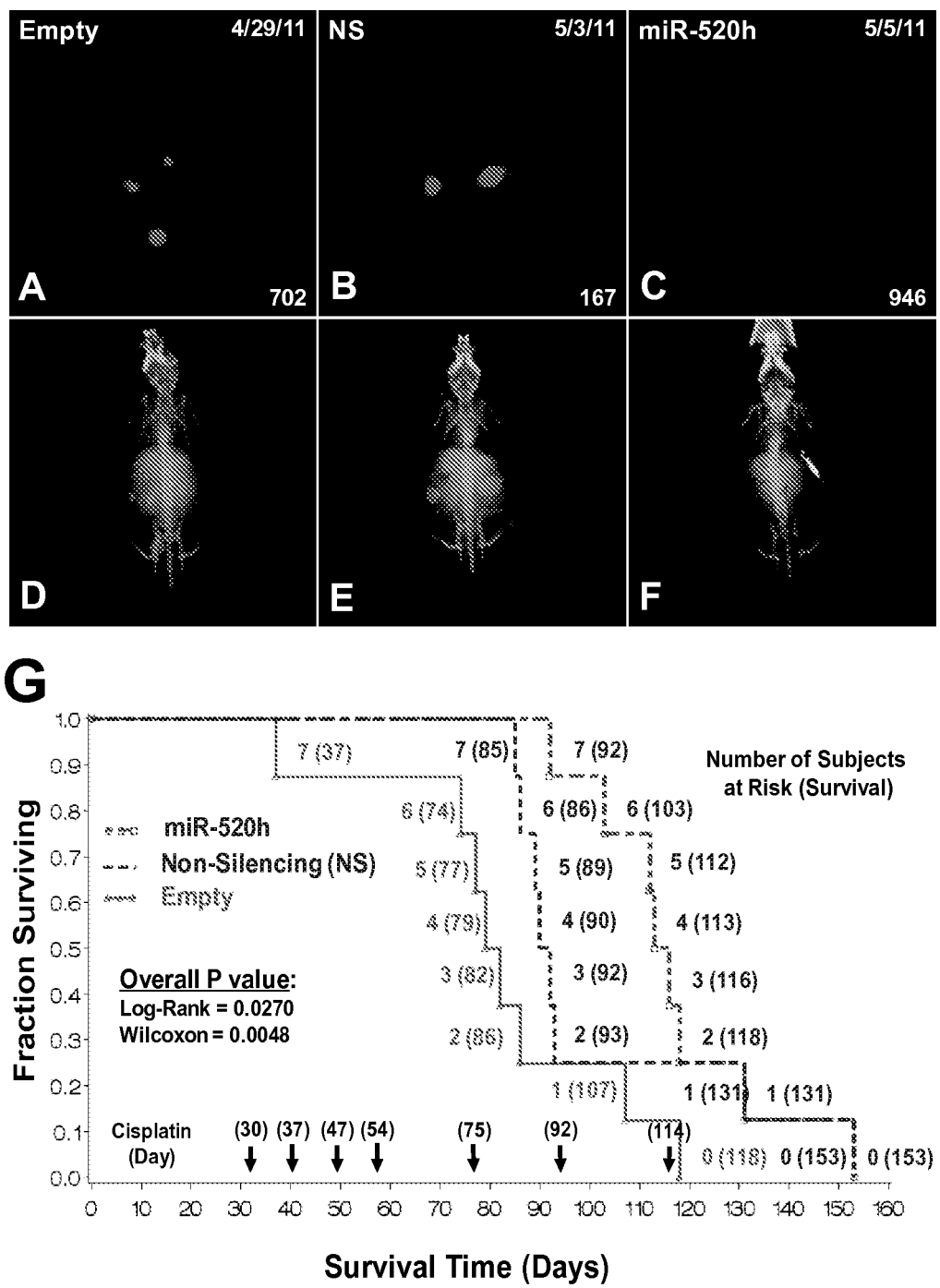
FIGS. 6A-G. Expression of miR-520g/h Improves Survival for Xenografted Animals. Survival analysis for Fox1$^{nu/nu}$ mice xenografted with 2.5×10$^6$ OVCAR8 cells expressing either mir-520g/h mimic, non-targeting mimic control or empty vector. Median survival for animals xenografted with miR-520g/h expressing cells is significantly longer (113 days) than animals xenografted with cells expressing either non-targeting microRNA mimic (90 days) or empy vector (79 days). Cisplatin doses were administered as noted.

To determine whether expression of miR-520h impacted responses of ovarian cancer xenografts to systemically administered chemotherapy, the inventors inoculated Fox1nu/nu mice with 4×10$^6$ OVCAR8 cells stably expressing either miR-520h mimic, a non-targeting mimic control or empty vector. Once tumor implants were readily palpable, weekly administration of cisplatin equivalent to a dose of 5 mg/kg was initiated and given weekly for a total of 4 weeks. This course of treatment was specifically used to mimic the typical course experienced by women undergoing treatment for this illness. Xenografts in experimental groups responded to this treatment regimen with a nearly complete elimination of disease in animal inoculated with OVCAR8 cells stably expressing miR-520h (FIGS. 6A-6F), whereas the low doses of cisplatin used in these experiments had much less impact on shrinking the tumor burden in control implants. This observation is consistent with a sensitization of ovarian cancer cells to cisplatin by miR-520h mimic. Cisplatin was continued approximately biweekly at a reduced dose of 1.5 mg/kg until disease progression requiring euthanasia of animals by IACUC criteria. As demonstrated in FIG. 6, the mean survival for animals xenografted with OVCAR8 cells stably expressing mir-520h was 114 days, an increase of ~44% when compared to control animals inoculated OVCAR8 cells stably expressing empty vector (FIG. 6G). In contrast, median survival for animals xenografted with OVCAR8 cells stably transfected with empty vector or OVCAR8 cells stably expressing non-targeting microRNA control was 79 days and 90 days, respectively. At necropsy, examination of these animals demonstrated that implants were significantly smaller in animals xenografted with OVCAR8 cells stably expressing miR-520h compared to either non-targeting mimic control or empty vector.

Mimics for miR-520g/h Impact Creation of Spheroids, a Key Intermediate in Metastasis and Cancer Stem Cells and Impact Patterns of Cancer Stemness.

OVCAR8 and SVOK3ip1 cells stably expressing mimics for miR-520h demonstrate decreased capacity to form spheroids, multicellular aggregates that play a key role in ovarian cancer metastasis. (FIG. 9A) Spheroids have also been used to isolate subpopulations of cells that fulfill many of the criteria of cancer stem cells and express enhanced levels of specific gene products including EZH2, OCT4 and NANOG associated with pleuripotency in human embryonic stem cells (16). (FIG. 9B) Expression of miR-520gh impacts patterns of and eliminates increased expression of specific patterns of gene expression (i.e. lin28A/B) associated with stemness that are induced when ovarian cancer cells (OVCAR8 and SKOV3ip1) are cultured in media that induce spheroid formation.

Example 4 miR-520H Sensitizes Cell Lines Derived from Uterine Cancer to Cisplatin

Figure 10:
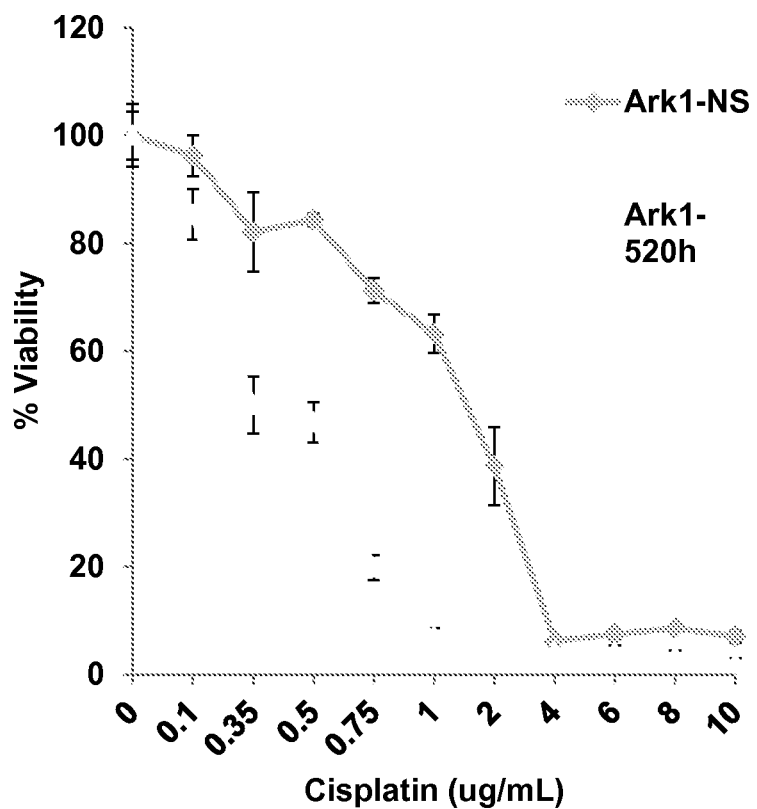
FIG. 10: miR-520h sensitizes cell lines derived from uterine cancer to cisplatin. UPSC Ark1 cells stably transfected with lentiviral vector driving the expression of either miR-520h or a non-targeting miRNA control were incubated with increasing concentrations of cisplatin. As demonstrated above, the IC50 for cisplatin was reduced by more than 90% in cells expressing miR-520h

FIG. 10 demonstrates that miR-520h sensitizes cell lines derived from uterine cancer to cisplatin. UPSC Ark1 cells stably transfected with lentiviral vector driving the expression of either miR-520h or a non-targeting miRNA control were incubated with increasing concentrations of cisplatin. As demonstrated in FIG. 10, the IC50 for cisplatin was reduced by more than 90% in cells expressing miR-520h.

Example 5

Significance of Embodiments of the Invention

Understanding molecular events critical for sensitizing ovarian cancers to the established cell-killing effects of platinum-based chemotherapy is an important goal not only for determining how best to initially treat women newly diagnosed with this disease but also reducing the toxicity associated with the use of platinum-based chemotherapy and potentially reversing the resistance that emerges with continue platinum treatment. Unfortunately, the molecular mechanisms responsible for platinum resistance in ovarian cancer remain poorly understood. Recently, a number of investigators have begun to examine this question at a molecular level, identifying multiple gene products potentially involved in the emergence of platinum resistance. Their efforts have pointed to a number of cell pathways, including the TGF-β signaling pathway as well as DNA damage repair pathways as playing a critical role in determining whether ovarian cancers respond to platinum-based chemotherapy (17-19, 21). Particularly interesting are observations that platinum-sensitivity is at least partly determined by patterns of gene expression that have been associated with mutations in the ovarian cancer susceptibility gene BRCA1 (22).

The role of microRNAs in determining the sensitivity of ovarian cancers to chemotherapy remains largely unexplored. The inventors screened known human microRNAs with the goal of identifying individual microRNAs potentially suitable for this goal. In certain aspects of the invention, microRNAs that remain silencing or whose expression may be lost or whose levels of expression are suppressed during the course of platinum-based treatment are useful targets for sensitizing ovarian cancers to chemotherapy. The inventors identified miRNA 520-a, g, and/or h that in certain embodiments of the invention undergo frequent copy number gains and loss in ovarian cancers. Despite this, levels of expression for the individual microRNAs encoded by this locus are typically quite low or not expressed. However, the data clearly establish that the ectopic expression of at least one exemplary microRNA, miR-520h, can be used to impact the biologic behavior of ovarian cancer both in vitro and in vivo, despite the fact that it is not expressed in ovarian cancer cell lines in which it has been tested. In part, miR-520h accomplishes this feat via the translational inhibition of ATM expression and increasing the rate at which this tumor suppressor is degraded, in certain embodiments. Other investigators have demonstrated that the generation of ΔATM in ovarian and other types of cancer cells are primarily due to Caspase 7 activity (23,24). However, it is not presently clear whether this also holds true for ovarian cancer cells treated with miR-520h as the results also indicate that Caspase 7 is a target for MiR-520h mediated gene silencing and that its expression to cisplatin treatment are blunted by the presence of miR-520h. In addition, in some embodiments miR-520h contributes to the sensitization of ovarian cancers by also targeting the expression of multiple, other oncogenes and tumor suppressors implicated in ovarian cancer and whose function has been shown to be involved not only in apoptosis, but also DNA damage repair.

The data also provide insight into the mechanisms by which ovarian cancers can be sensitized to cisplatin. miR-520h sensitize both p53-mutated OVCAR8 cells and p53- null SKOV3ip1 cells. However, miR-520h appears to sensitize p53-null SKOV3ip1 cells to a much greater degree than p53-mutated OVCAR8 cells. In addition, the inventors see very different apoptotic responses in these two cell lines in response to platinum treatment in the presence and absence of miR-520h. The differences in the rates of apoptosis observed in response to cisplatin in OVCAR8 and SKOV3ip1 cells are not necessarily surprising given that these two cells lines have very different patterns of p53 expression, for example. In specific embodiments, differences in apoptotic response in OVCAR8 and SKOV31ip1 cells are because of the differences in the p53 status of these two different ovarian cancer cell lines.

The observations have identified a number of individual microRNAs useful as therapeutic targets in at least ovarian cancer. The results contribute significantly to understanding of whether or how microRNAs can be used for therapeutic purposes. These observations indicate that the mechanisms are susceptible in a novel approach differently from how many investigators are currently considering the use of microRNAs as therapeutic targets in human disease.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

Remington's Pharmaceutical Sciences, 18th Ed. Mack Printing Company, 1990.

1. Rose P G, Mossbruger K, Fusco N, Smrekar M, Eaton S, Rodriguez M. Gemcitabine reverses cisplatin resistance: demonstration of activity in platinum- and multidrug-resistant ovarian and peritoneal carcinoma. Gynecologic oncology. 2003; 88:17-21.

2. Rose P G, Blessing J A, Mayer A R, Homesley H D. Prolonged oral etoposide as second-line therapy for platinum-resistant and platinum-sensitive ovarian carcinoma: a Gynecologic Oncology Group study. Journal of clinical oncology: official journal of the American Society of Clinical Oncology. 1998; 16:405-10.

3. Mutch D G, Orlando M, Goss T, Teneriello M G, Gordon A N, McMeekin S D, et al. Randomized phase III trial of gemcitabine compared with pegylated liposomal doxorubicin in patients with platinum-resistant ovarian cancer. Journal of clinical oncology: official journal of the American Society of Clinical Oncology. 2007; 25:2811-8.

4. Markman M, Blessing J, Rubin S C, Connor J, Hanjani P, Waggoner S. Phase II trial of weekly paclitaxel (80 mg/m2) in platinum and paclitaxel-resistant ovarian and primary peritoneal cancers: a Gynecologic Oncology Group study. Gynecologic oncology. 2006; 101:436-40.

5. Sehouli J, Stengel D, Harter P, Kurzeder C, Belau A, Bogenrieder T, et al. Topotecan Weekly Versus Conventional 5-Day Schedule in Patients With Platinum-Resistant Ovarian Cancer: a randomized multicenter phase II trial of the North-Eastern German Society of Gynecological Oncology Ovarian Cancer Study Group. Journal of clinical oncology: official journal of the American Society of Clinical Oncology. 2011; 29:242-8.

6. Gordon A N, Tonda M, Sun S, Rackoff W. Long-term survival advantage for women treated with pegylated liposomal doxorubicin compared with topotecan in a phase 3 randomized study of recurrent and refractory epithelial ovarian cancer. Gynecologic oncology. 2004; 95:1-8.

7. Morgan R J, Jr., Alvarez R D, Armstrong D K, Boston B, Burger R A, Chen L M, et al. NCCN Clinical Practice Guidelines in Oncology: epithelial ovarian cancer. J Natl Compr Canc Netw. 2011; 9:82-113.

8. O'Malley D M, Azodi M, Makkenchery A, Tangir J, McAlpine J, Kelly M, et al. Weekly topotecan in heavily pretreated patients with recurrent epithelial ovarian carcinoma. Gynecologic oncology. 2005; 98:242-8.

9. O'Malley D M, Richardson D L, Rheaume P S, Salani R, Eisenhauer E L, McCann G A, et al. Addition of bevacizumab to weekly paclitaxel significantly improves progression-free survival in heavily pretreated recurrent epithelial ovarian cancer. Gynecologic oncology. 2011; 121:269-72.

10. Cohn D E, Fabbri M, Valeri N, Alder H, Ivanov I, Liu C G, et al. Comprehensive miRNA profiling of surgically staged endometrial cancer. Am J Obstet Gynecol. 2010; 202:656 e1-8.

11. Iorio M V, Ferracin M, Liu C G, Veronese A, Spizzo R, Sabbioni S, et al. MicroRNA gene expression deregulation in human breast cancer. Cancer Research. 2005; 65:7065-70.

12. Yanaihara N, Caplen N, Bowman E, Seike M, Kumamoto K, Yi M, et al. Unique microRNA molecular profiles in lung cancer diagnosis and prognosis. Cancer Cell. 2006; 9:189-98.

13. Nagaraja A K, Creighton C J, Yu Z, Zhu H, Gunaratne P H, Reid J G, et al. A link between mir-100 and FRAP1/mTOR in clear cell ovarian cancer. Mol Endocrinol. 2010; 24:447-63.

14. Xin M, Small E M, Sutherland L B, Qi X, McAnally J, Plato C F, et al. MicroRNAs miR-143 and miR-145 modulate cytoskeletal dynamics and responsiveness of smooth muscle cells to injury. Genes & development. 2009; 23:2166-78.

15. van Rooij E, Sutherland L B, Qi X, Richardson J A, Hill J, Olson E N. Control of stress-dependent cardiac growth and gene expression by a microRNA. Science. 2007; 316:575-9.

16. Livak K J, Schmittgen T D. Analysis of relative gene expression data using real-time quantitative PCR and the 2(-Delta Delta C(T)) Method. Methods (San Diego, Calif. 2001; 25:402-8.

17. Livak K J, Schmittgen T D. Analysis of relative gene expression data using real-time quantitative PCR and the 2(-Delta Delta C(T)) Method. Methods (San Diego, Calif. 2001; 25:402-8.

18. Rose P G, Mossbruger K, Fusco N, Smrekar M, Eaton S, Rodriguez M. Gemcitabine reverses cisplatin resistance: demonstration of activity in platinum- and multidrug-resistant ovarian and peritoneal carcinoma. Gynecologic oncology. 2003; 88:17-21.

2. Rose P G, Blessing J A, Mayer A R, Homesley H D. Prolonged oral etoposide as second-line therapy for platinum-resistant and platinum-sensitive ovarian carcinoma: a Gynecologic Oncology Group study. Journal of clinical oncology: official journal of the American Society of Clinical Oncology. 1998; 16:405-10.

3. Mutch D G, Orlando M, Goss T, Teneriello M G, Gordon A N, McMeekin S D, et al. Randomized phase III trial of gemcitabine compared with pegylated liposomal doxorubicin in patients with platinum-resistant ovarian cancer. Journal of clinical oncology: official journal of the American Society of Clinical Oncology. 2007; 25:2811-8.

4. Markman M, Blessing J, Rubin S C, Connor J, Hanjani P, Waggoner S. Phase II trial of weekly paclitaxel (80 mg/m2) in platinum and paclitaxel-resistant ovarian and primary peritoneal cancers: a Gynecologic Oncology Group study. Gynecologic oncology. 2006; 101:436-40.

5. Sehouli J, Stengel D, Harter P, Kurzeder C, Belau A, Bogenrieder T, et al. Topotecan Weekly Versus Conventional 5-Day Schedule in Patients With Platinum-Resistant Ovarian Cancer: a randomized multicenter phase II trial of the North-Eastern German Society of Gynecological Oncology Ovarian Cancer Study Group. Journal of clinical oncology: official journal of the American Society of Clinical Oncology. 2011; 29:242-8.

6. Gordon A N, Tonda M, Sun S, Rackoff W. Long-term survival advantage for women treated with pegylated liposomal doxorubicin compared with topotecan in a phase 3 randomized study of recurrent and refractory epithelial ovarian cancer. Gynecologic oncology. 2004; 95:1-8.

7. Morgan R J, Jr., Alvarez R D, Armstrong D K, Boston B, Burger R A, Chen L M, et al. NCCN Clinical Practice Guidelines in Oncology: epithelial ovarian cancer. J Natl Compr Canc Netw. 2011; 9:82-113.

8. O'Malley D M, Azodi M, Makkenchery A, Tangir J, McAlpine J, Kelly M, et al. Weekly topotecan in heavily pretreated patients with recurrent epithelial ovarian carcinoma. Gynecologic oncology. 2005; 98:242-8.

9. O'Malley D M, Richardson D L, Rheaume P S, Salani R, Eisenhauer E L, McCann G A, et al. Addition of bevacizumab to weekly paclitaxel significantly improves progression-free survival in heavily pretreated recurrent epithelial ovarian cancer. Gynecologic oncology. 2011; 121:269-72.

10. Cohn D E, Fabbri M, Valeri N, Alder H, Ivanov I, Liu C G, et al. Comprehensive miRNA profiling of surgically staged endometrial cancer. Am J Obstet Gynecol. 2010; 202:656 e1-8.

11. Iorio M V, Ferracin M, Liu C G, Veronese A, Spizzo R, Sabbioni S, et al. MicroRNA gene expression deregulation in human breast cancer. Cancer Research. 2005; 65:7065-70.

12. Yanaihara N, Caplen N, Bowman E, Seike M, Kumamoto K, Yi M, et al. Unique microRNA molecular profiles in lung cancer diagnosis and prognosis. Cancer Cell. 2006; 9:189-98.

13. Nagaraja A K, Creighton C J, Yu Z, Zhu H, Gunaratne P H, Reid J G, et al. A link between mir-100 and FRAP1/mTOR in clear cell ovarian cancer. Mol Endocrinol. 2010; 24:447-63.

14. Xin M, Small E M, Sutherland L B, Qi X, McAnally J, Plato C F, et al. MicroRNAs miR-143 and miR-145 modulate cytoskeletal dynamics and responsiveness of smooth muscle cells to injury. Genes & development. 2009; 23:2166-78.

15. van Rooij E, Sutherland L B, Qi X, Richardson J A, Hill J, Olson E N. Control of stress-dependent cardiac growth and gene expression by a microRNA. Science. 2007; 316:575-9.

16. Zhang S, Balch C, Chan M W, Lai H C, Matei D, Schilder J M, et al. Identification and characterization of ovarian cancer-initiating cells from primary human tumors. Cancer Research. 2008; 68:4311-20.

17. Livak K J, Schmittgen T D. Analysis of relative gene expression data using real-time quantitative PCR and the 2(-Delta Delta C(T)) Method. Methods (San Diego, Calif. 2001; 25:402-8.

18. Gong F, Peng X, Zeng Z, Yu M, Zhao Y, Tong A. Proteomic analysis of cisplatin resistance in human ovarian cancer using 2-DE method. Mol Cell Biochem. 2011; 348:141-7.

19. Glaysher S, Gabriel F G, Johnson P, Polak M, Knight L A, Parker K, et al. Molecular basis of chemosensitivity of platinum pre-treated ovarian cancer to chemotherapy. British Journal of Cancer. 2010; 103:656-62.

20. Kim A, Serada S, Enomoto T, Naka T. Targeting annexin A4 to counteract chemoresistance in clear cell carcinoma of the ovary. Expert Opin Ther Targets. 2010; 14:963-71.

21. Carey M S, Agarwal R, Gilks B, Swenerton K, Kalloger S, Santos J, et al. Functional proteomic analysis of advanced serous ovarian cancer using reverse phase protein array: TGF-beta pathway signaling indicates response to primary chemotherapy. Clinical cancer research: an official journal of the American Association for Cancer Research. 2010; 16:2852-60.

22. Konstantinopoulos P A, Spentzos D, Karlan B Y, Taniguchi T, Fountzilas E, Francoeur N, et al. Gene expression profile of BRCAness that correlates with responsiveness to chemotherapy and with outcome in patients with epithelial ovarian cancer. Journal of clinical oncology: official journal of the American Society of Clinical Oncology. 2010; 28:3555-61.

23. Wang J, Pabla N, Wang C Y, Wang W, Schoenlein P V, Dong Z. Caspase-mediated cleavage of ATM during cisplatin-induced tubular cell apoptosis: inactivation of its kinase activity toward p53. Am J Physiol Renal Physiol. 2006; 291:F1300-7.

24. Smith G C, d'Adda di Fagagna F, Lakin N D, Jackson S P. Cleavage and inactivation of ATM during apoptosis. Molecular and Cellular Biology. 1999; 19:6076-84.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of sensitizing ovarian cancer in an individual to a cancer treatment that is platinum-based chemotherapy, comprising the step of administering to the individual an effective amount of a composition as follows:
 a RNA polynucleotide comprising SEQ ID NO:1, SEQ ID NO:2, or SEQ ID NO:3,
 wherein upon administering the composition to the individual, the ovarian cancer is thereby sensitized to the platinum-based chemotherapy treatment.

2. The method of claim 1, wherein the composition is delivered to the individual by liposome, nanosphere, nanoparticle, nanodiamonds, impregnated polymer, multistage nanoparticles and/or gels.

3. The method of claim 1, wherein the composition is delivered to the individual intravenously or intraperitoneally.

4. The method of claim 1, wherein the composition is delivered to the individual prior to the cancer treatment.

5. The method of claim 1, wherein the composition is delivered to the individual subsequent to the cancer treatment.

6. The method of claim 1, wherein the composition is delivered to the individual concomitantly with the cancer treatment.

7. The method of claim 1, wherein the treatment is cisplatin.

* * * * *